(12) United States Patent
Shadduck

(10) Patent No.: US 12,324,500 B2
(45) Date of Patent: *Jun. 10, 2025

(54) SYSTEMS AND METHODS FOR TREATING LIPS AND SKIN

(71) Applicant: Hermes Innovations, LLC, San Jose, CA (US)

(72) Inventor: John H. Shadduck, Menlo Park, CA (US)

(73) Assignee: John H. Shadduck, Menlo Park, CA (US)

( * ) Notice: Subject to any disclaimer, the term of this patent is extended or adjusted under 35 U.S.C. 154(b) by 310 days.

This patent is subject to a terminal disclaimer.

(21) Appl. No.: 17/222,773

(22) Filed: Apr. 5, 2021

(65) Prior Publication Data

US 2022/0312934 A1 Oct. 6, 2022

(51) Int. Cl.
| | | |
|---|---|---|
| *A61H 7/00* | (2006.01) | |
| *A45D 34/04* | (2006.01) | |
| *A61H 9/00* | (2006.01) | |
| *A61H 15/00* | (2006.01) | |
| *A61M 35/00* | (2006.01) | |
| *B05C 1/12* | (2006.01) | |

(52) U.S. Cl.
CPC ............ *A45D 34/041* (2013.01); *A61H 7/00* (2013.01); *B05C 1/12* (2013.01); *A45D 2200/1036* (2013.01); *A45D 2200/20* (2013.01); *A61H 7/008* (2013.01); *A61H 9/0057* (2013.01); *A61H 15/00* (2013.01); *A61H 2015/0064* (2013.01); *A61M 35/00* (2013.01)

(58) Field of Classification Search
CPC .......... A61H 9/0057; A61H 2015/0064; A61H 2201/10; A61H 7/00; A61H 7/001; A61H 7/002; A61H 7/003; A61H 7/008; A61H 2007/009

See application file for complete search history.

(56) References Cited

U.S. PATENT DOCUMENTS 2,574,601 A * 11/1951 Swanson ................. A61H 7/003
601/123
4,883,047 A * 11/1989 Guitay ............... A61H 15/0092
601/123
6,090,055 A * 7/2000 Frajdenrajch .......... A61H 7/008
15/384

(Continued)

OTHER PUBLICATIONS

English translation of Sanchez (WO 01/39717 A1) (Year: 2001).*
English translation of Serge (FR 2659851 A1) (Year: 1991).*

*Primary Examiner* — Tu A Vo
*Assistant Examiner* — Christopher E Miller
(74) *Attorney, Agent, or Firm* — Levine Bagade Han LLP

(57) ABSTRACT

Methods and devices for treating a targeted tissue including a skin or a lip and more particularly methods and devices that enhances absorption of treatment media into tissue for cosmetic and therapeutic purposes, where applicators for treating the targeted tissue are configured to apply negative pressure with an aspiration portion having a plurality of apertures distributed over the aspiration portion, and the distal tip of the applicator has a low friction surface such that the distal tip of the applicator is configured to contact the targeted tissue to apply the negative pressure while maintaining a low friction surface against the targeted tissue.

20 Claims, 32 Drawing Sheets

(56) References Cited

U.S. PATENT DOCUMENTS

| | | | |
|---|---|---|---|
| 6,299,620 B1 * | 10/2001 | Shadduck | A61B 17/54 604/289 |
| 6,585,667 B1 * | 7/2003 | Muller | A61H 7/008 601/6 |
| 6,641,591 B1 * | 11/2003 | Shadduck | A61B 17/545 606/131 |
| 6,679,856 B2 | 1/2004 | Mueller | |
| 6,743,215 B2 | 6/2004 | Bernabei | |
| 7,497,635 B1 * | 3/2009 | Bae | A45D 34/04 401/188 R |
| 8,048,089 B2 | 11/2011 | Ignon et al. | |
| 8,262,592 B1 | 9/2012 | Brooks et al. | |
| 8,579,837 B1 * | 11/2013 | Makower | A61H 23/0263 601/6 |
| 8,814,836 B2 | 8/2014 | Ignon et al. | |
| 8,939,669 B2 | 1/2015 | Le et al. | |
| 2001/0037118 A1 * | 11/2001 | Shadduck | A61B 17/545 606/131 |
| 2002/0016601 A1 * | 2/2002 | Shadduck | A61B 17/545 606/131 |
| 2003/0014081 A1 * | 1/2003 | Bernabei | A61H 7/008 607/3 |
| 2004/0073144 A1 * | 4/2004 | Carava | A61H 9/005 601/6 |
| 2004/0208683 A1 * | 10/2004 | Shawan | A61H 15/0092 401/6 |
| 2004/0220622 A1 * | 11/2004 | Bernabei | A61N 1/0476 607/3 |
| 2004/0260209 A1 * | 12/2004 | Ella | A61H 19/32 601/7 |
| 2004/0260210 A1 * | 12/2004 | Ella | A61H 33/08 601/7 |
| 2005/0119594 A1 * | 6/2005 | Piana | A61H 7/008 601/19 |
| 2006/0100555 A1 * | 5/2006 | Cagle | A61H 23/0254 601/63 |
| 2007/0027411 A1 * | 2/2007 | Ella | A61H 9/005 601/7 |
| 2007/0239173 A1 * | 10/2007 | Khalaj | A61B 17/545 606/131 |
| 2007/0249975 A1 * | 10/2007 | Pan | A61H 15/0092 601/123 |
| 2008/0200778 A1 * | 8/2008 | Taskinen | A61H 7/005 601/134 |
| 2008/0221504 A1 * | 9/2008 | Aghion | A61N 1/40 604/20 |
| 2010/0010401 A1 * | 1/2010 | Tudico | A61H 9/005 601/118 |
| 2012/0150079 A1 * | 6/2012 | Rosenberg | A61H 7/008 601/6 |
| 2013/0110014 A1 * | 5/2013 | Luzon | A61H 9/0057 601/6 |
| 2014/0343481 A1 * | 11/2014 | Ignon | A61M 5/3298 604/21 |
| 2015/0088050 A1 * | 3/2015 | Chang | A61N 1/327 604/20 |
| 2015/0196452 A1 | 7/2015 | Meyer et al. | |
| 2015/0328081 A1 * | 11/2015 | Goldenberg | A61H 23/02 600/38 |
| 2015/0360014 A1 * | 12/2015 | Decaux | A45D 34/04 604/20 |
| 2016/0038183 A1 * | 2/2016 | Ignon | A61B 50/22 606/131 |
| 2016/0051436 A1 * | 2/2016 | Rosario | A61H 7/008 601/6 |
| 2016/0128605 A1 * | 5/2016 | Moreno | A61H 7/008 601/6 |
| 2016/0256671 A1 * | 9/2016 | Ignon | A61B 17/54 |
| 2016/0324295 A1 * | 11/2016 | Lee | A61H 15/0092 |
| 2017/0056281 A1 * | 3/2017 | Yi | A61N 5/0616 |
| 2017/0056636 A1 * | 3/2017 | Shadduck | A61H 9/0057 |
| 2017/0224972 A1 * | 8/2017 | Ignon | A61M 37/00 |
| 2018/0161233 A1 * | 6/2018 | Nakanishi | A61N 1/322 |
| 2018/0303515 A1 | 10/2018 | Shadduck et al. | |
| 2019/0029917 A1 * | 1/2019 | George | A61H 7/008 |
| 2020/0179220 A1 * | 6/2020 | Jablow | A61H 1/00 |
| 2022/0313537 A1 | 10/2022 | Shadduck | |

\* cited by examiner

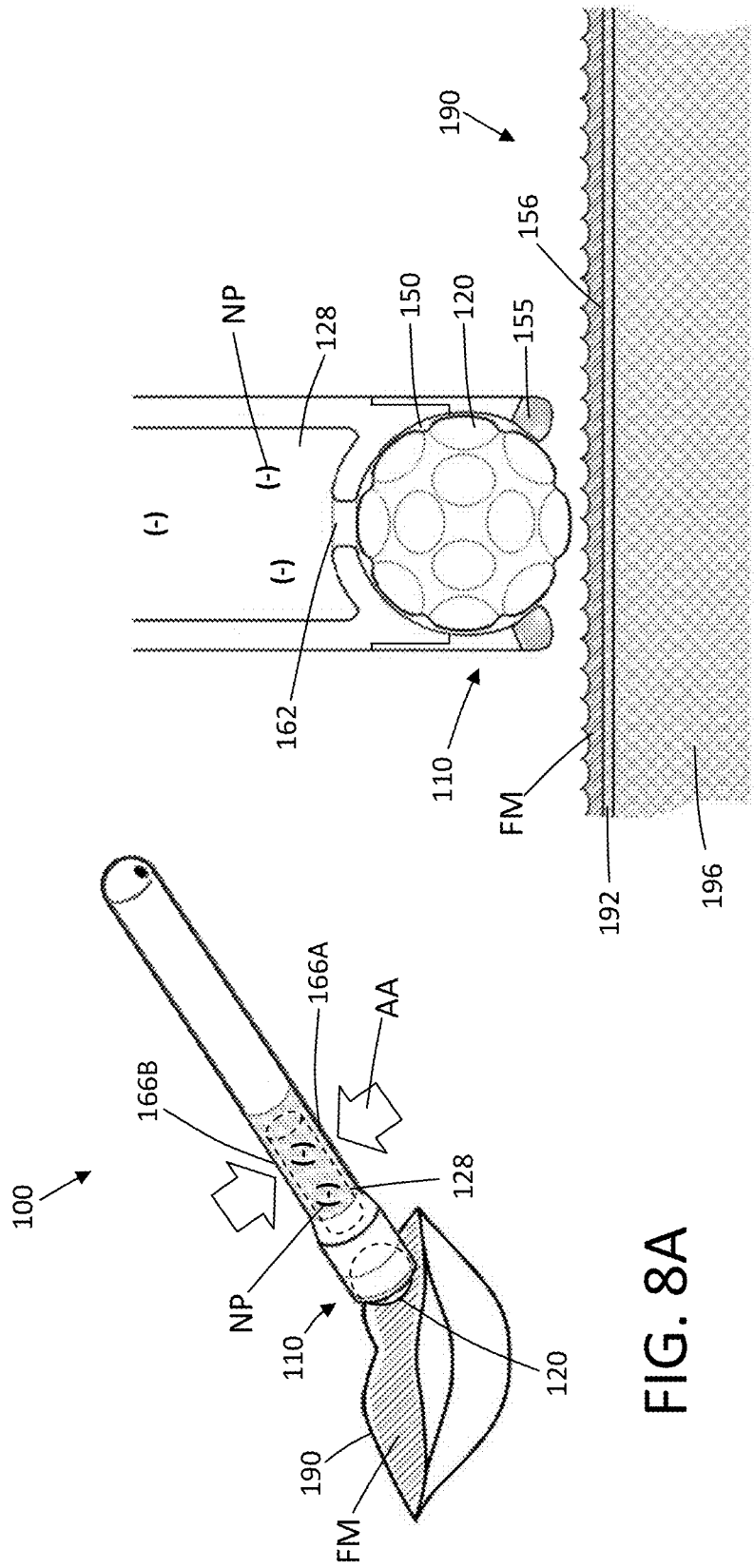

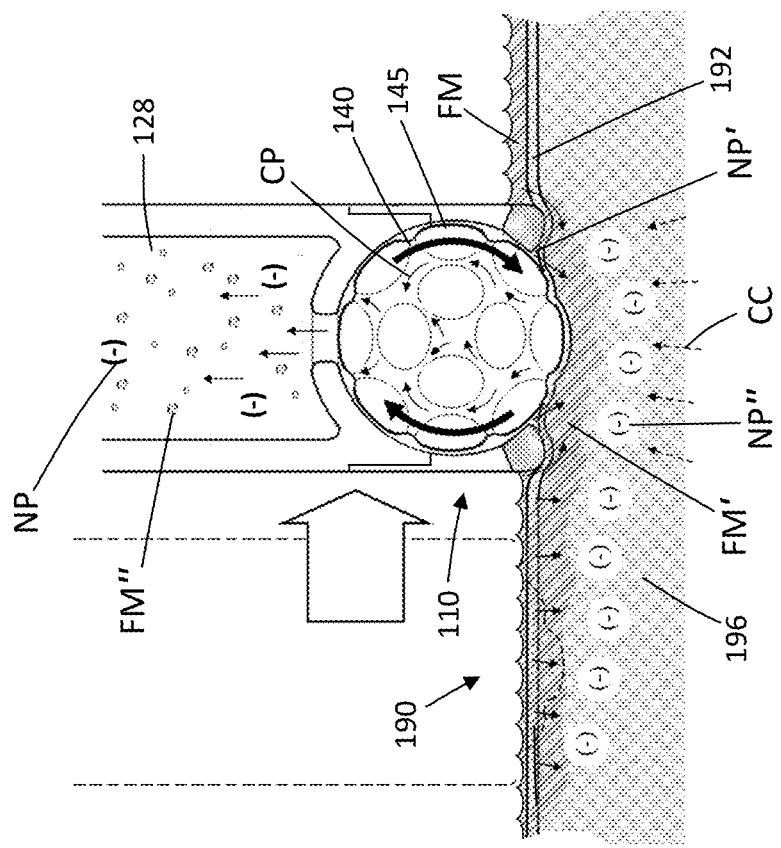
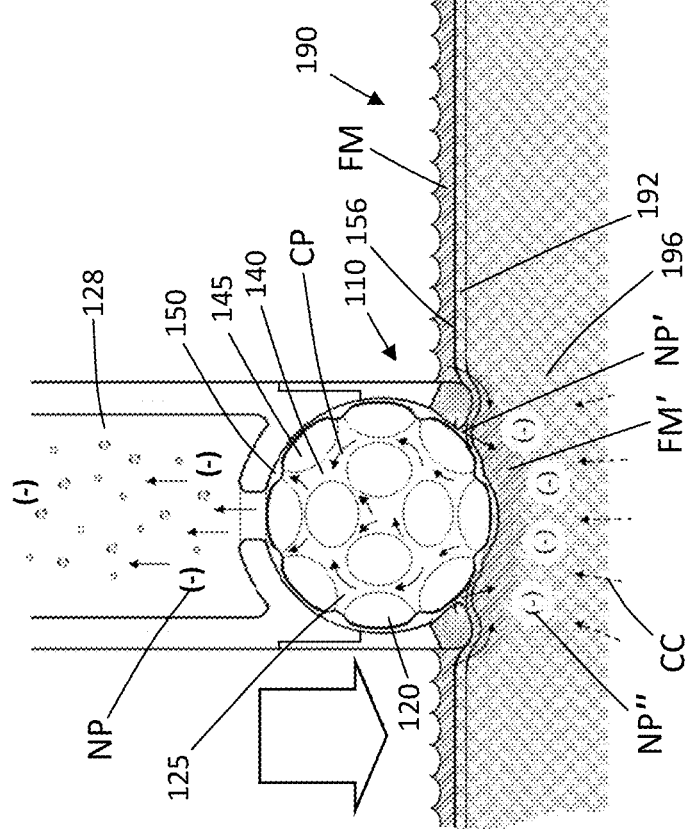
FIG. 8D
FIG. 8C

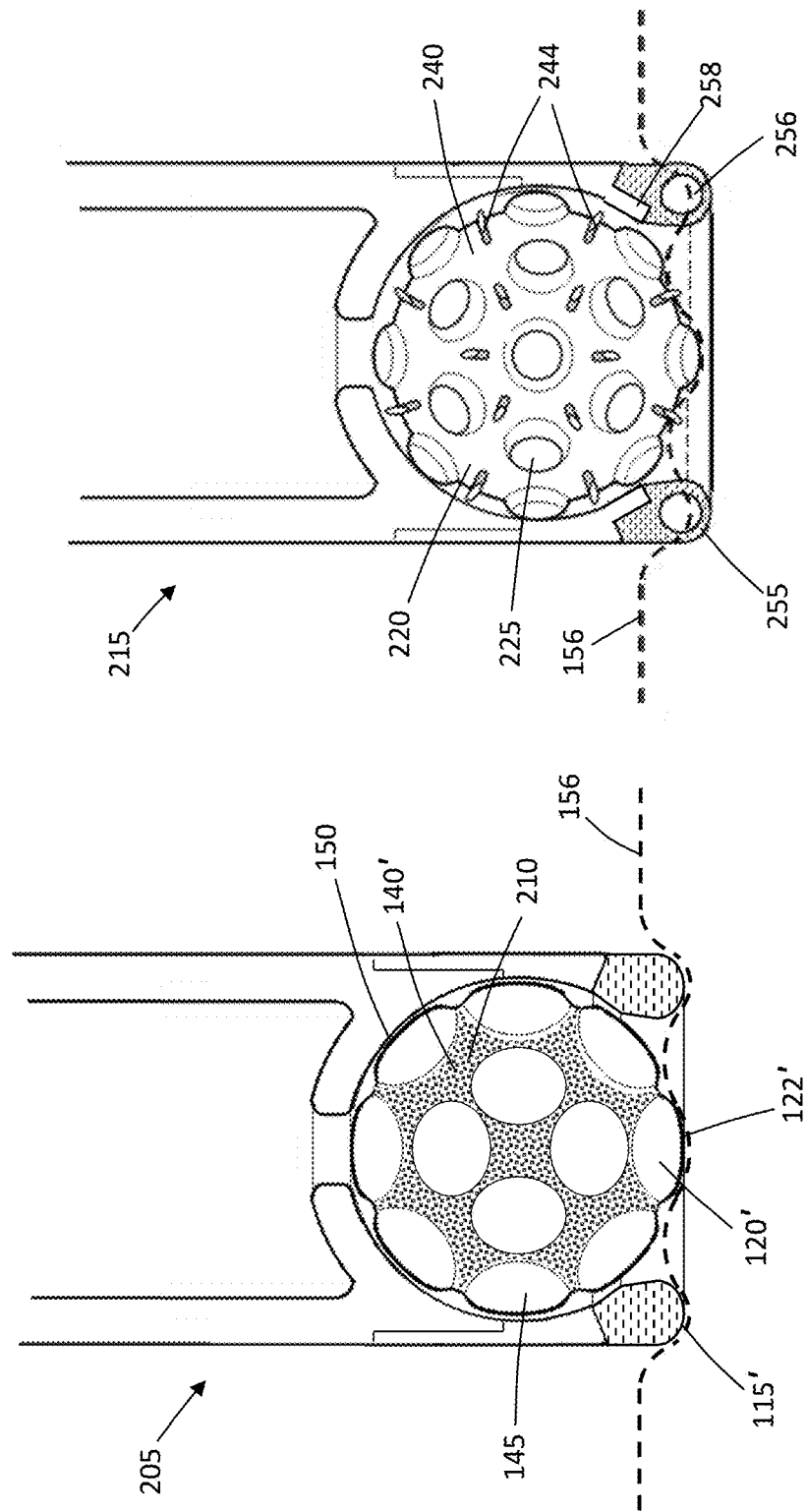

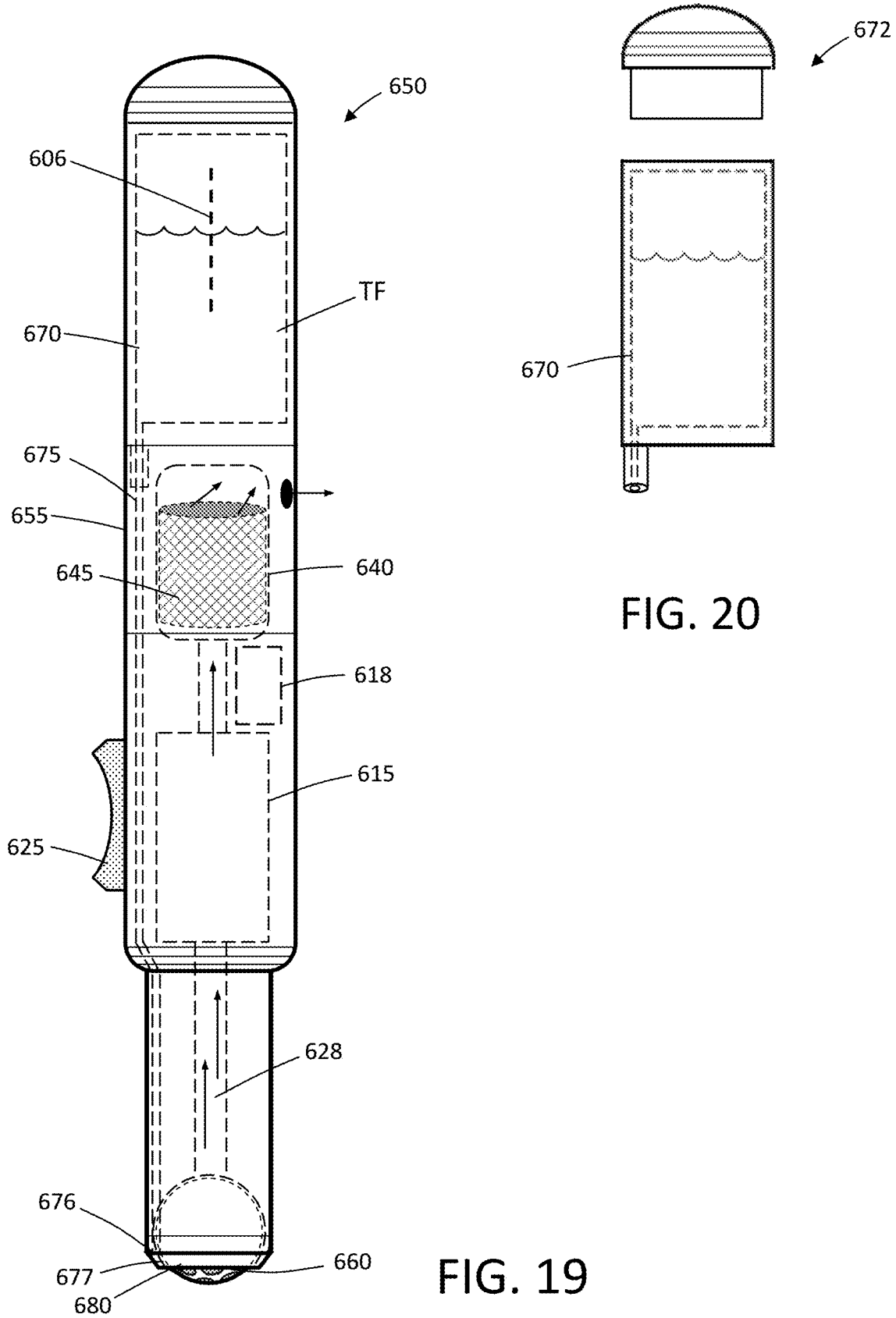

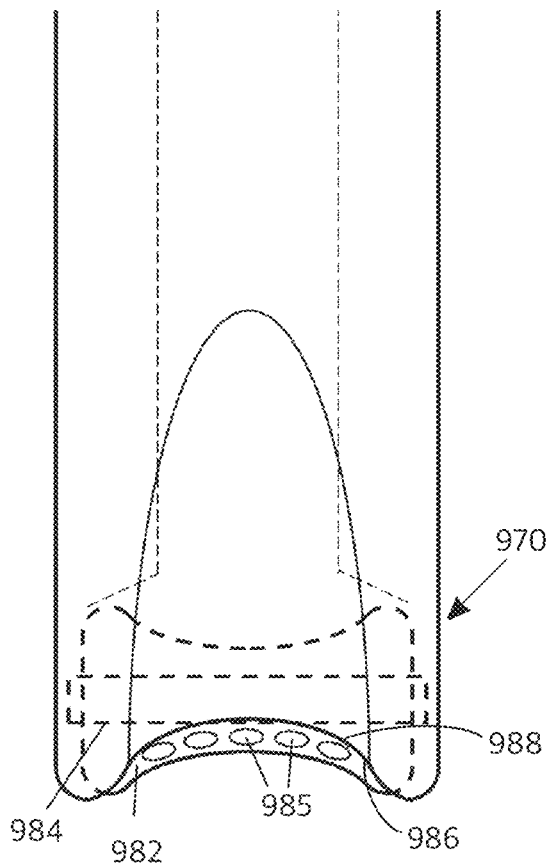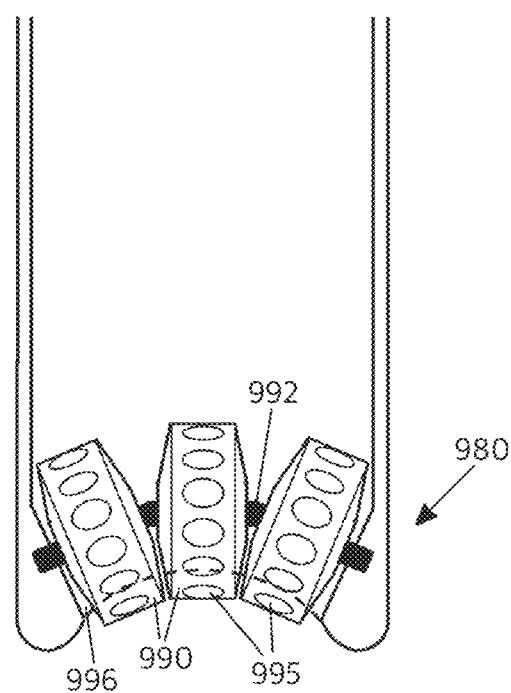
FIG. 36
FIG. 37

SYSTEMS AND METHODS FOR TREATING LIPS AND SKIN

BACKGROUND

The present invention relates to methods and devices for treating a subject's skin or lips and more particularly methods and devices that enhances absorption of treatment media into tissue for cosmetic and therapeutic purposes.

SUMMARY OF THE INVENTION

The applicator systems and methods corresponding to the invention relate in general to the fields of skin care, hair restoration and lip care wherein the systems may be used by an individual for infusing treatment media into his or her skin or lips for cosmetic and rejuvenation purposes, hair restoration purposes or other therapeutic purposes.

The present disclosure includes devices for enhancing fluid delivery to a subject's skin or lips. For example, one variation of such a device includes an applicator body extending about a longitudinal axis from a proximal end to a distal applicator tip; a rolling member carried in a receiving space of the applicator tip; and a negative pressure mechanism communicating with a flow pathway in the applicator tip for applying negative pressure to tissue engaged by the applicator tip.

A variation of the device can include the applicator body having a distal periphery and where the rolling member and the distal periphery are configured to contact tissue during use. The distal periphery can be configured to create a seal against the tissue during use.

In an additional variation, an exposed portion of the rolling member extends distally from the distal periphery less than 25% of the diameter of the rolling member.

Variations of the rolling member can have a non-smooth surface. Alternatively, or in combination, the surface of the rolling member can be a first surface portion defining a spherical rotational envelope and a second surface portion comprising surface discontinuities. The flow pathway can comprise the surface discontinuities in the rolling member. In some variations, the surface discontinuities comprise at least one of recesses, channels, grooves, notches, facets, bores and porosities.

Variations of the device can include the first surface portion defining a selected surface area that allows the rolling member to roll smoothly in a cooperating surface of the receiving space. In some examples, the first surface portion has surface area of at least 40% of the surface area of said spherical rotational envelope of the rolling member.

The variations of the device can include a second surface portion having a surface area of at least 10% of the surface area of said spherical rotational envelope of the rolling member.

In additional variations, the surface of the rolling member can include recessed portions and adjacent projecting portions. Variations of the projecting portions can have a sharp apex. Alternatively, or in combination, a projecting portion can comprise a needle. In yet additional variations, at least a portion of the rolling member has an abrasive surface.

The devices described herein can include a distal periphery that comprises at least one of a resilient material and a lubricious material. The distal periphery can also include an abrasive surface.

The negative pressure mechanisms used herein can comprise any vacuum source. For example, one variation includes a positive displacement pump. In additional variations, the negative pressure mechanism is adapted for manual actuation.

The devices described herein can further comprise a valve in the flow pathway.

In additional variations, the devices can have an applicator body that includes at least first and second detachable elements that when detached allow for removal of the rolling member.

Variations of the applicators can carry at least one LED and a rolling member that is at least partly transparent material.

The devices can also include flow pathway, which comprises surface discontinuities in surface of the receiving space.

The invention described herein also includes methods for treating a subject's skin or lips. For example, one such method includes contacting a tissue surface with a rolling member carried at a distal end of an applicator body; moving the rolling member over the tissue surface; and creating negative pressure about the rolling member in contact with the tissue surface to transiently cause negative pressure in subsurface tissue to enhance permeability of the tissue surface.

The methods described herein can further include applying a treatment media to the tissue surface. In some variations, the moving step manipulates tissue to thereby enhance penetration of the treatment media therein. Alternatively, or in combination, the moving step includes the surface discontinuities of the rolling member causing at least one of compressing, stretching, tensioning and piercing the tissue surface.

In an additional variation, the method includes a creating step, which suctions treatment media in a circuitous path over the tissue surface about the surface discontinuities to thereby enhance penetration of the treatment media therein.

The methods can also include a distal periphery of the applicator body that contacts tissue to seal the negative pressure around the rolling member as it moves over the tissue surface.

In another variation of a method, the moving step abrades the tissue surface with an abrasive surface of the applicator body to thereby enhance penetration of the treatment media therein.

The present disclosure also includes methods for treating a targeted tissue. For example, such a method can include a targeted tissue that comprises a skin or a lip of a subject. However, any tissue region can be treated by variations of the devices and methods described herein.

In one variation, a method for treating a targeted tissue includes providing an applicator capable of applying a negative pressure within the applicator, wherein a distal tip of the applicator has a perimeter portion surrounding an aspiration portion having a plurality of apertures distributed over the aspiration portion, the distal tip further comprising a low friction surface; contacting the targeted tissue of the skin or the lip with the distal tip of the applicator while maintaining the low friction surface against the targeted tissue; and applying the negative pressure and moving the distal tip over the targeted tissue to transiently cause negative pressure in a subsurface tissue where the low friction surface reduces a friction of the distal tip against the targeted tissue.

The present disclosure also includes devices for treating a targeted tissue. In one example, such a device includes an applicator body carrying a negative pressure source for providing a negative pressure within the applicator body;

and a distal tip of the applicator body having a perimeter portion configured for contacting the targeted tissue, wherein the perimeter portion surrounds an aspiration portion, the aspiration portion having a plurality of apertures distributed over the aspiration portion such that a surface of the aspiration portion between the plurality of apertures comprises a non-apertured field, and wherein plurality of apertures are configured to apply with the negative pressure to the targeted tissue; and wherein the plurality of apertures are distributed over the aspiration portion to distribute the negative pressure over all regions of the aspiration portion exposed in the perimeter portion that interface with the targeted tissue.

The methods and devices described herein can include variations where the aspiration portion comprises a rolling member rotatably located within the distal tip and where the plurality of apertures extend through the rolling member such that the rolling member located between the plurality of apertures comprises the low friction surface, wherein moving the distal tip over the targeted tissue causes rotation of the rolling member against tissue and reduces friction between the distal tip and the targeted tissue. The rolling member can roll about a single axis or can rotate in a 360-degree direction.

Variations of the methods and device include a low friction surface that comprises a lubricious material located on the perimeter portion.

The aspiration portions can have a surface area of at least 25 mm2 and the plurality of apertures can each have a width of 2.00 mm or less. In those variations where the apertures are not symmetric, the width of 2.00 mm can be measured across a minor axis.

Variations of the devices and method can be equipped with one or more electrodes that are configured to apply a current into targeted tissue to cause electroporation of the tissue thereby increasing permeability and allowing passage of a substance through of a surface of the targeted tissue. The devices and methods can administer any substance to produce a desired therapeutic or other effect. For example, such a substance can include a hyaluronic acid, moisturizer, numbing agent, etc. The methods and devices can also include applying a topical treatment media to the surface of the targeted tissue.

The methods and devices can apply a negative pressure at the distal tip when in contact with tissue during use that is at least negative 3.0 psi. Moreover, controlling of the negative pressure can use a controller in the applicator coupled to a negative pressure source. Alternatively, the controller can be external to the applicator and coupled thereto by a wire or wireless connection. Variations of the controller can be responsive to signals from a pressure sensor carried by the applicator that senses negative pressure within the applicator during use. In additional variations, controllers can be configured to control the negative pressure source to maintain a selected negative pressure within the applicator during use.

The controllers can also be responsive to signals from an accelerometer carried by the applicator to modulate or terminate negative pressure in the applicator during use when lack of movement is detected. Additional variations include controllers configured with a time-out feature that stops the negative pressure source after a selected interval of use followed by a selected time-out interval after which the negative pressure source may be activated. The controllers can be configured to pulse the negative pressure source. The controllers can be configured to provide a limit to negative pressure within the applicator body during use and/or to maintain a selected negative pressure within the applicator body during use.

In additional variations, a controller is configured with a time-out feature that stops activation of the negative pressure source after a selected interval of use followed by a selected time-out interval after which the negative pressure source may be re-activated.

The methods and devices described herein can further include use of a mobile electronic device to communicate with the controller through a wireless connection to a bluetooth-type receiver carried by the applicator to adjust operating parameters of the applicator. Variations of the methods and devices can include using a blue-tooth type transmitter carried by the applicator to transmit operating data to a remote electronic device or a cloud storage.

The devices and methods can also include use of an applicator where the perimeter portion comprises a sponge-like material.

The negative pressure sources can be positioned within the applicator or can be external to the applicator. Any type of negative pressure source can be used. One such example includes a motor driven pump.

Additional variations of the devices include those with a tip having a shape selected from a group of round, oval, rectangular, polygonal and hour-glass shaped. In additional variations, the device can include a surface of perimeter portion has a planar configuration. Alternatively, the surface of perimeter portion can have a non-planar configuration.

It will be understood that other objects and purposes of the invention, and variations thereof, will be apparent upon reading the following specification and inspecting the accompanying drawings. These and other features, aspects and advantages of the present invention will become better understood with reference to the following drawings.

BRIEF DESCRIPTION OF THE DRAWINGS

FIG. 8A illustrates a first step in a method of the invention where the subject applies a treatment media topically to lips and actuates the squeeze bulb to create negative pressure in the applicator.

FIG. 8B illustrates an enlarged view of the step in the method of FIG. 8A where the applicator tip is prepared for contact with flowable treatment media applied topically to the tissue surface.

FIG. 8C illustrates a subsequent step of the method where applicator tip is pressed into contact with the tissue surface which applies negative pressure about the rolling member and to the tissue surface as well as causing negative pressure within subsurface tissue to further cause absorption of the treatment media.

FIG. 8D illustrates a subsequent step where the applicator tip is translated across the tissue surface which continues to apply negative pressure about the rolling member that causes negative pressure in subsurface tissues which in turn causes absorption and penetration of the treatment media into the tissue.

FIG. 9 is a cut-away view of another variation of applicator tip similar to that of FIG. 1 where the rolling member includes abrasive portions for providing traction with tissue.

FIG. 10 is a cut-away view of yet another variation of applicator tip similar to that of FIG. 1 where the rolling member includes sharp micro-needles for providing traction with tissue and for causing penetrations in surface tissue.

FIG. 19 is an elevational view of another variation of an applicator with a distal rolling member wherein the applicator body carries a DC motor driven pump assembly, a filter, and a detachable fluid reservoir for carrying a treatment fluid.

FIG. 20 is an elevational view of the detachable fluid reservoir of FIG. 19.

FIG. 36 is an elevational view of another applicator tip configured with hour-glass shaped rolling member and a cooperating non-planar distal-facing periphery.

FIG. 37 is a sectional view of anther applicator tip with a non-planar distal-facing periphery and a plurality of rolling members that rotate about an axle.

DETAILED DESCRIPTION OF THE INVENTION

Figure 1:
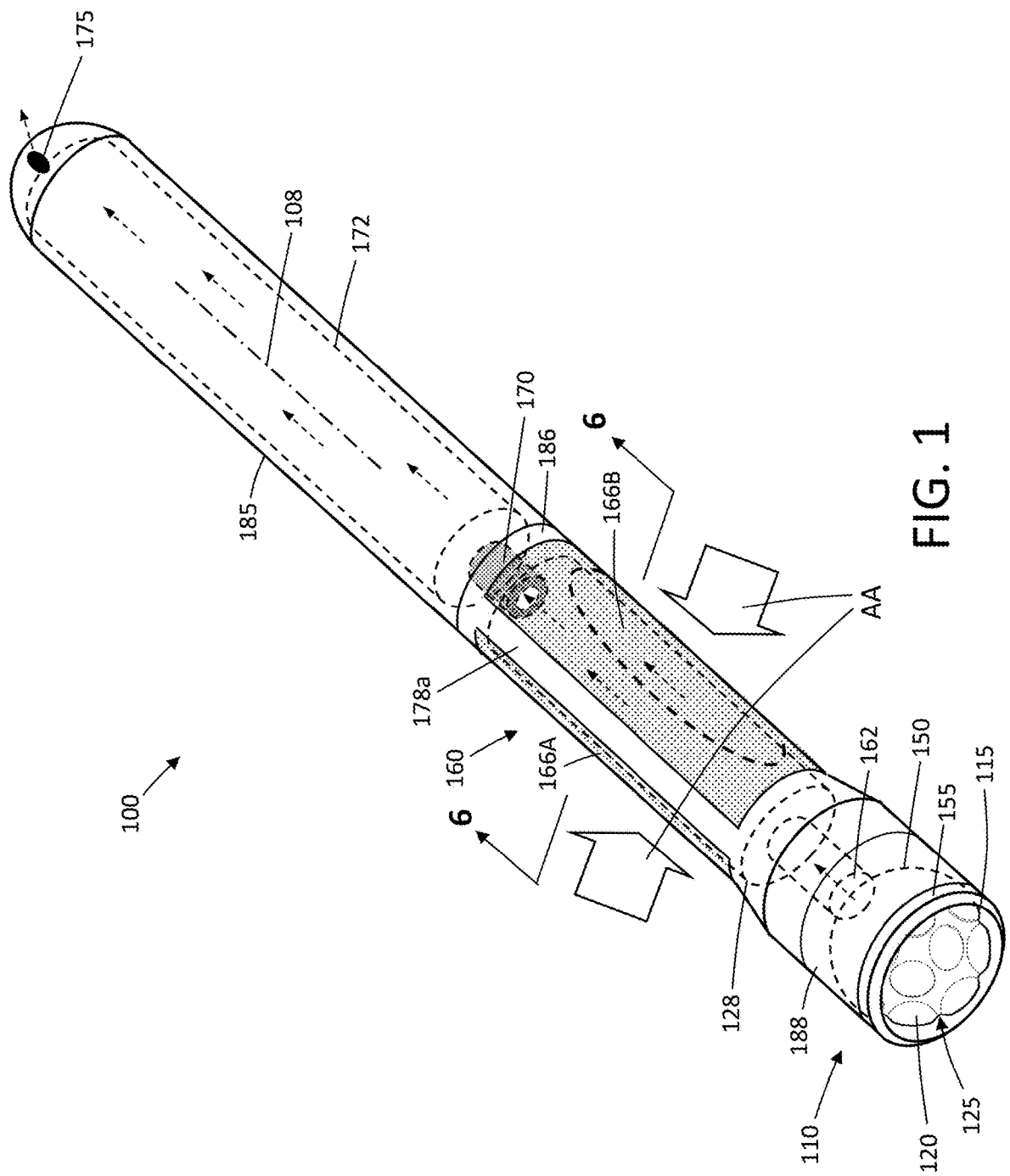
FIG. 1 is a perspective view of an embodiment of a treatment device or applicator corresponding to the invention adapted for enhancing fluid absorption by a subject's lips or skin, where a distal applicator tip includes a rolling member surrounded by a peripheral tissue-contacting element.

FIGS. 1, 3 and 5A-5B illustrate a system for treating skin or lips which comprises a hand-held treatment device or applicator 100 with a distal applicator tip 105 that is adapted for applying transient negative pressure to a skin surface to enhance fluid absorption and penetration into surface layers of a treatment site in a subject's skin or lips. The device or applicator 100 has a shaft or applicator body 106 extending about longitudinal axis 108 that is gripped with a subject's fingers for movement over a treatment site. The distal applicator tip or roller tip 105 defines a skin interface where the applicator body 106 has a distal housing 110 with a distal periphery 115 that surrounds or is adjacent to an exposed portion of a rolling member 120. As will be described below, the distal periphery 115 is configured to provide a seal against a tissue surface for the purpose of containing negative pressure around the rolling member 120 when in contact with a targeted treatment site.

As background, roller ball devices are well known in the art for applying cosmetic fluids, deodorants and the like to skin with a spherical roller ball that carries fluid from an interior chamber of an applicator to a skin surface as the roller ball contacts and rolls over a treatment site. As an example, FIG. 2 illustrates a typical prior art cosmetics roller ball as shown in U.S. Pat. No. 8,939,669 issued Jan. 27, 2015 to Son Q. Le et al, titled "Roller-Ball Applicator Assembly for Topical Oils Application" (see FIG. 1B in '669 with original reference numerals removed for convenience). As can be seen in FIG. 2, an important aspect of such prior art roller ball devices can be understood wherein the roller ball has a diameter D and the axial dimension A of the "exposed surface" (in sectional view) of the roller ball extends well beyond the distal tip of the device housing H and is a substantial fraction of the roller ball diameter D (referents D, A and H added by the author to the prior art figure). The large dimension A of the "exposed surface" of the roller ball is important for carrying fluids and applying such fluids to a subjects' skin. In such cosmetic roller ball applicators, the "exposed surface" dimension A as shown in FIG. 2 typically ranges from 25% to 40% of the roller ball diameter D. In such a prior art roller ball devices, the roller is exposed to an interior chamber of the assembly that carries a treatment liquid. Such a liquid interfaces with a surface of a rotating roller ball and the can apply a film of the liquid to a subject's skin. As will be described below, the present invention differs entirely in that (i) there is no liquid contained in a chamber or channel that interfaces with the roller ball, and thus (ii) there is no liquid delivered by the roller ball to a subject's skin. In contrast, the present invention has an interior channel that interfaces with the rolling member, where such an interior channel communicates with a negative pressure source to suction or aspirate fluid around or through the rolling member into such an interior channel. This system allows the rolling member to be configured for skin manipulation rather than liquid delivery to a skin surface.

Figure 2:
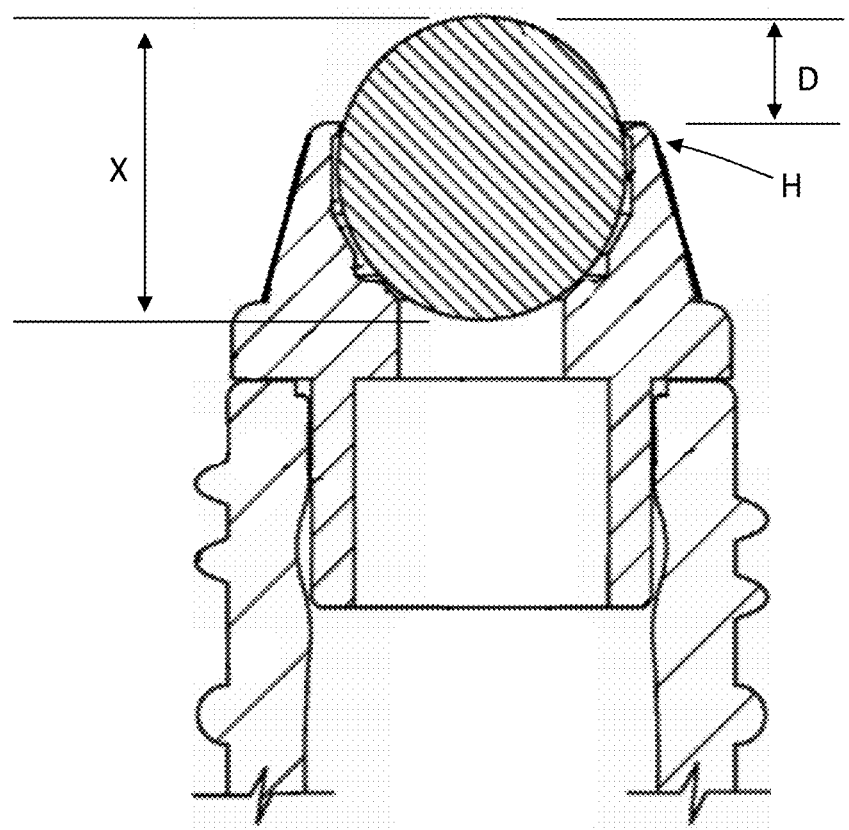
FIG. 2 is a sectional view of a prior art cosmetic roller ball device.
Figure 3:
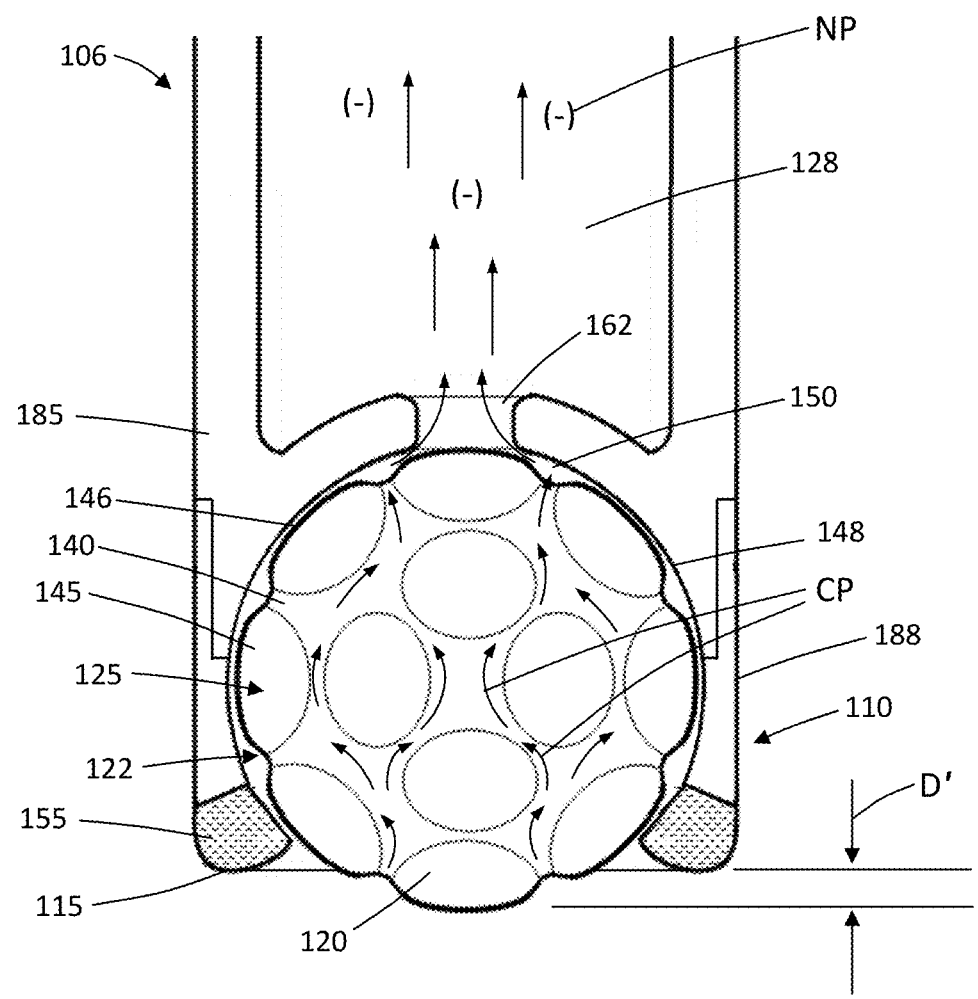
FIG. 3 is an enlarged cut-away view of the applicator tip of FIG. 1 showing the rolling member with discontinuities in the surface thereof for manipulating engaged tissue and for causing a circuitous path of fluid flows over a tissue surface when the rolling member is in contact with tissue.

Now turning to FIG. 3, a distal applicator tip 105 of the present invention is shown. As can be seen in FIG. 3, the applicator tip 105 carries a rolling member 120 in housing 110 that has a function that is entirely different from that of prior art cosmetic roller ball devices as in FIG. 2. In FIG. 3, the distal roller tip 105 is configured to apply negative pressure to a tissue surface—not a fluid. The fluid absorption aspect of the invention is a resulting effect of the negative pressure delivered to, and contained within, the distal applicator tip 105 when engaging a tissue surface. In the variation shown in FIG. 3, the rolling member 120 is not configured to contact and deliver fluid from an interior channel 128 of the device. The function of the rolling member 120 of the invention is to manipulate tissue in contact with the rolling member 120 which thereby allows fluid absorption and penetration into the tissue surface. The term tissue manipulation as used herein describes the effects of the rolling surface 122 of rolling member 120 that is configured with surface discontinuities 125 that engage tissue, where the effects can be described as, or include, stretching or tensioning tissue, compressing tissue, piercing tissue, indenting tissue or otherwise transiently modifying tissue from its natural state to a manipulated state as the surface discontinuities 125 of rolling member 120 engage the tissue surface under negative pressure to thereby transiently and locally increase the permeability of the skin surface layer. Of particular interest, the rolling member 120 thus is adapted to create the desired tissue manipulation effects in a friction-free manner as the rolling surface 122 and surface discontinuities 125 roll over a tissue surface.

Referring again to FIG. 3, the enlarged view of the rolling member 120 shows a rolling surface 122 that is not smooth but is configured surface discontinuities 125 that comprise first and second surface portions where the second surface consists of recessed portions or channels 140 around the first surface portion consisting of projecting portions 145. The recessed portions 140 provide a flow path for negative pressure NP in interior channel 128 to flow around the surface 122 of the rolling member 120. As will be described below, the negative pressure NP when in sealed contact with the patient's lips or skin can cause transient negative pressure within the engaged tissue to assist in rapid absorption or penetration of a fluid media into the engaged tissue. In the variation shown in FIG. 3, the rolling member 120 has a plurality of projecting portions 145 that may number from 10 to 1,000 or more where the outermost surfaces 146 of the projecting portions 145 define a spherical rotational envelope. Such outermost surface 146 rollably contacts the surface 148 of the receiving space 150 in the distal housing 110 of the applicator tip 105 that receives the rolling member 120. The term "spherical rotational envelope" as used herein describes the envelope in which the rolling member 120 contacts if it were rotated in all possible directions. As can be understood from FIG. 3, the number of projecting portions 145 are of a sufficient number to ensure that the rolling member 120 rolls or rotates smoothly in the receiving space 150. Typically, the first surface portion consisting of projecting portions 145 has surface area of at least 40% of the total surface area of the spherical rotational envelope of the rolling member 120. Further, the second surface portion consisting of the recessed portions 140 has a surface area of at least 10% of the total surface area of the spherical rotational envelope of the rolling member 120.

Still referring to FIG. 3, the surface discontinuities 125 are shown as channels, but other features can provide suitable flow pathways and fall within the scope of the invention, which includes notches, facets, recesses, grooves, partial bores, through-bores and porosities. Further, the projecting portions 145 may have outermost surfaces 146 that vary within a rolling member 120, for example, with some outermost surfaces 146 being flatter to allow smooth rotation and other outermost surfaces 146 having a sharp apex or a needle-like tip to penetrate tissue or to indent and stretch a tissue surface. As can be understood from FIG. 3, in one variation, the recessed portions or channels 140 are interconnected to thus provide circuitous pathways CP for aspirated fluid flows about the surface of the rolling member 120. Thus, when the rolling member 120 is in contact with tissue, a fluid treatment media under such negative pressure is drawn through the circuitous pathways CP to thereby cause such a fluid media to remain in contact with the tissue surface for a longer interval compared to a non-circuitous pathway. Thus, the surface discontinuities 125 are specifically configured to manipulate the tissue surface and provide a circuitous flow pathway, where the tissue manipulation can consist of stretching, indenting or tensioning tissue, compressing tissue, and piercing or penetrating tissue. At the same time, as will be described below, the negative pressure at the tissue surface can cause transient negative pressure in subsurface tissue to cause the rapid absorption and penetration of the fluid media into the engaged tissue.

Still referring to FIG. 3, in a variation, the distal housing 110 of applicator body 106 has a distal peripheral element 155 that defines the distal periphery 115 where the peripheral element 155 comprises a lubricious material such as Teflon or a resilient material such as silicone, or a combination of lubricious and resilient materials, suited for providing a seal against tissue as the distal periphery 115 and rolling member 120 are translated over a tissue surface to thereby contain negative pressure in the interface of the tissue and the distal applicator tip 105.

In FIG. 3, it also can be seen that the housing 110 of the present invention differs from a typical cosmetic roller ball device as in the prior art device of FIG. 2. In FIG. 3, the exposed portion of rolling member 120 extends distally beyond distal periphery 115 of the housing 110 a dimension D' which is much smaller than dimension D in the prior art device of FIG. 2. In FIG. 3, the exposed portion of rolling member 120 extends distally from distal periphery 115 less than 25% of the diameter of the rolling member 120, and often less than 20% of the diameter of the rolling member 120. In a variation, the exposed portion of rolling member 120 extends distally from distal periphery 115 less than 10% of the diameter of the rolling member 120. It can be understood that dimension D' is important so that the surface 122 of the rolling member 120 and discontinuities 125 therein contact and manipulate tissue while the distal periphery 115 contacts and provides a seal to capture the negative pressure about the skin surface and cause negative pressure in subsurface tissue as will be described further below. In another aspect, the exposed surface of the rolling member 120 extends distally from distal periphery 115 less than 5 mm and often is less than 3 mm.

Figure 4:
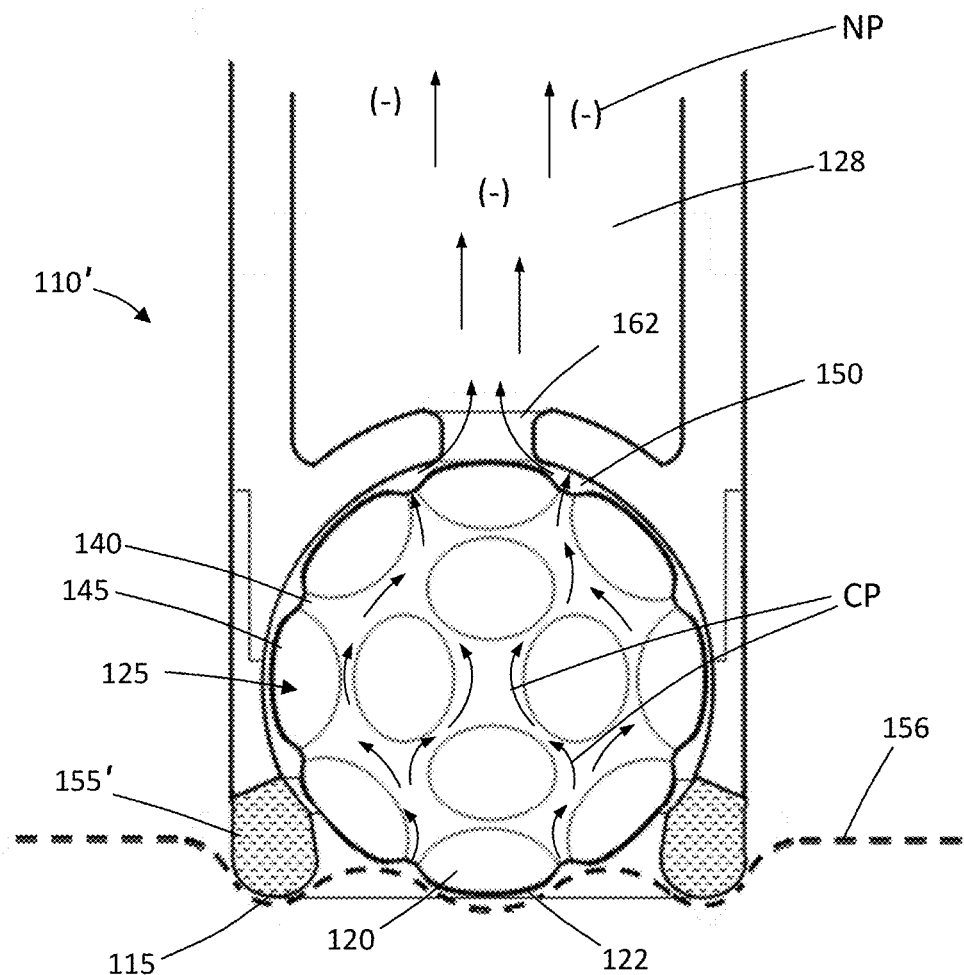
FIG. 4 is a cut-away view of a variation of an applicator tip similar to that of FIG. 3.

FIG. 4 illustrates a variation of a distal applicator tip 110' where the surface 122 of the rolling member 120 does not extend distally beyond the distal periphery 115. In this variation, the peripheral element 155' is extended distally further than the embodiment of FIG. 3. In all other aspects, the components and feature of the variations of FIGS. 3 and 4 are the same. In FIG. 4, the tissue surface 156 is shown in phantom view as the distal periphery 115 is pressed into tissue and negative pressure NP in the interior channel 128 of the distal tip 105 provides negative NP' at the tissue surface 156 captured within the distal periphery 115. The negative pressure NP' then suctions the tissue surface 156 into contact with the surface 122 of the rolling member 120.

Referring to FIGS. 1 and 3, the applicator body 106 can have any suitable dimension about axis 108 and any shape suited for gripping with a human hand or fingers. Typically, the rolling member 120 can have a diameter ranging from 3 mm to 20 mm and often has a diameter ranging from 5 mm to 10 mm. Devices with rolling members 120 having a smaller diameter are suited for treating lips and larger rolling members are suited for treating facial skin or other skin surfaces. The components of the applicator 100 can be understood from FIGS. 1 and 3 and the body 105 is fabricated of a molded plastic, metal, a combination of plastic and metal or other suitable materials. The body 106 can be a combination of single-use or limited-use components together with non-disposable components. In a variation, the applicator body 106 can be a transparent or translucent plastic material which allows for viewing of the interior thereof during use.

Figure 5A:
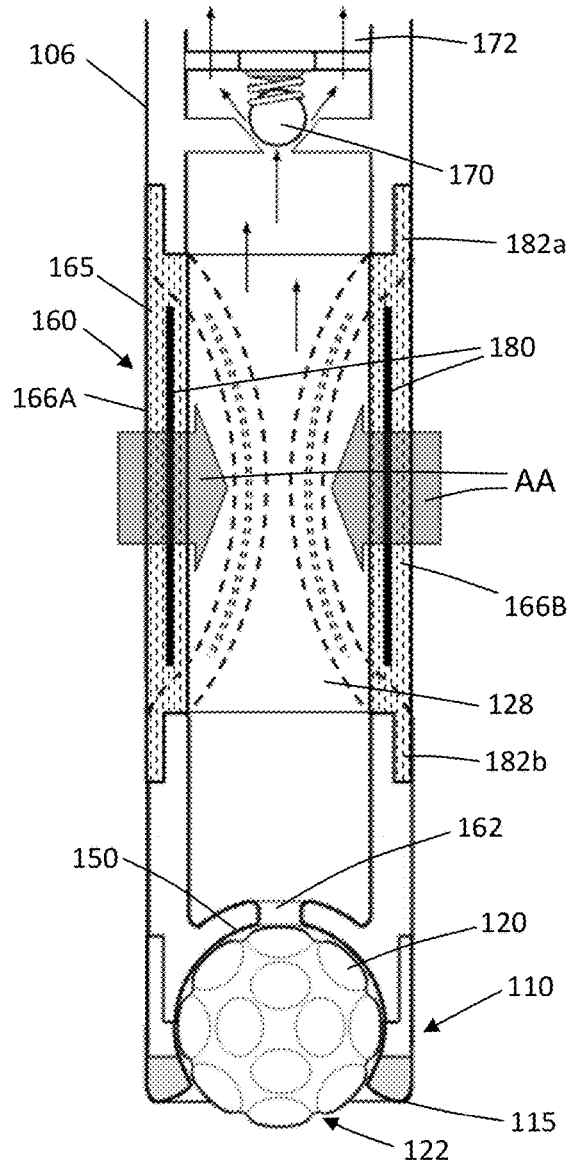
FIG. 5A is a sectional view of portion of the applicator body of the device of FIG. 1 showing a squeeze bulb component of the device in a first repose position, where the squeeze bulb is adapted to provide negative pressure in an interior channel of the device.
Figure 5B:
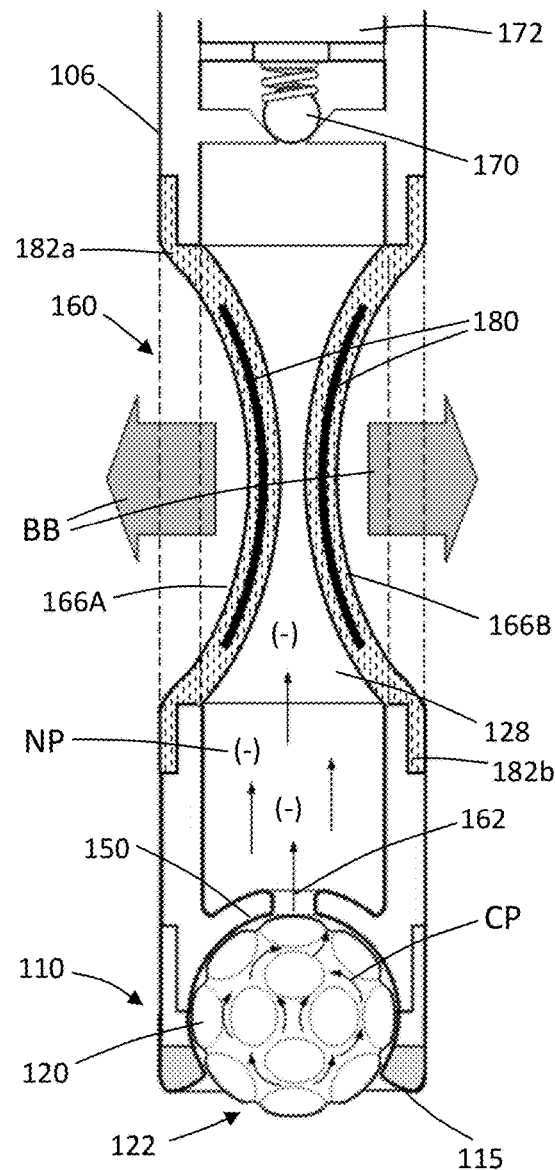
FIG. 5B is a sectional view of the applicator of FIG. 5A showing the squeeze bulb component in a second compressed and tensioned position, where the squeeze bulb when released from compression provides negative pressure in the interior channel of the device.
Figures 6, 7:
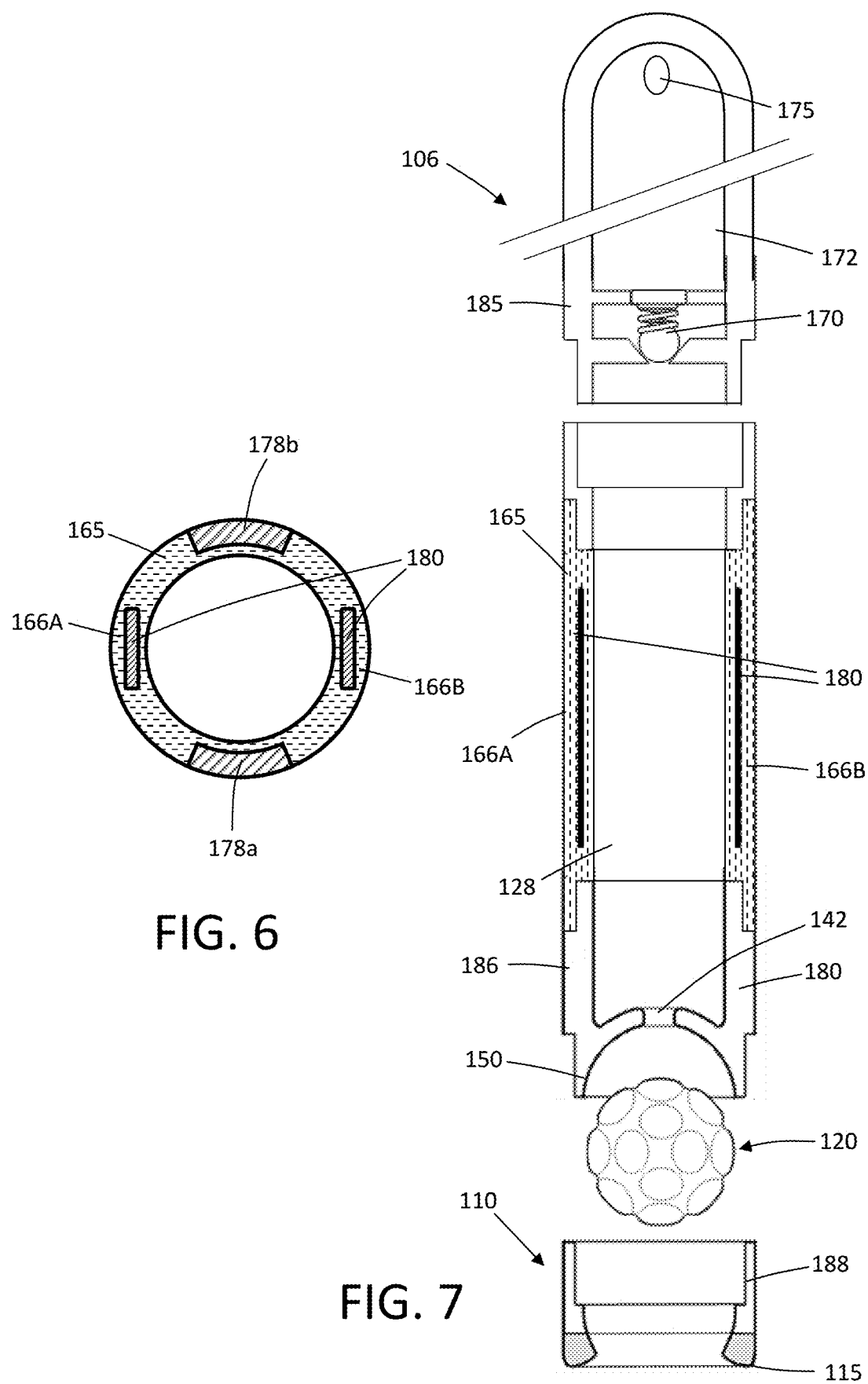
FIG. 6 is a sectional view of the applicator body taken along section 6-6 of FIG. 1.
FIG. 7 is an exploded view of the components of the device of FIG. 1 showing the various components de-mated from one another to allow for cleaning or replacement.

Referring now to FIGS. 1, 3 and 5A-5B, it can be seen that the applicator 100 includes a manually actuated negative pressure mechanism 160 in an interior aspiration chamber or channel 128 of the applicator 100 where the channel 128 has a distal end 162 that interfaces with the receiving space 150 around the rolling member 120 to apply negative pressure or suction around the rolling member 120 and to the targeted treatment site. In the device 100 as shown in FIGS. 1, 5A and 5B, the negative pressure mechanism 160 comprises an elastomeric squeeze bulb 165 where first and second sides 166A and 166B of the squeeze-bulb 165 are adapted to be pressed inwardly toward axis 108 which then causes air in the interior channel 128 to exit the channel 128 in the proximal direction through one-way valve 170 and thereafter through exit channel 172 in the proximal portion of the body to exit port 175 in the applicator body 106 (see FIGS. 1 and 7). As can be seen in FIGS. 1 and 6, the device body 106 has axial beam portions 178a and 178b that extend longitudinally as a support for the body 106 about the elastomeric squeeze bulb 165. In a variation, the squeeze bulb 165 has longitudinal leaf springs 180 molded into its elastomeric walls to urge the squeeze bulb 165 to the non-collapsed, linear shape as shown in FIGS. 1 and 5A. The proximal and distal ends (182a, 182b) of the elastomeric squeeze bulb 165 are bonded to the adjacent sections of the tubular body 106 to provide a sealed interior channel 128 (FIG. 5A).

In the variation shown in FIGS. 5A and 5B, a single leaf spring 180 is shown in each side of the squeeze bulb 165, but it should be appreciated that a plurality of spring elements can be used in each side 166A and 166B of the squeeze bulb. Alternatively, the spring elements may be disposed in the interior channel 128 and not fully embedded in the wall of the elastomeric squeeze bulb 165. In such an alternative, such leaf springs would then have a proximal and distal end that are fixed to the device body 106. It should be appreciated that other forms of spring elements may be used in a squeeze bulb structure such as collapsible-expandable braided structures, helical springs, zig-zag springs, and the like. In a variation, the elastomer of the squeeze bulb 165 can be a transparent or translucent material to allow viewing of the interior thereof during use.

FIGS. 5A and 5B illustrate a method of operating the negative pressure mechanism 160. In FIG. 5A, the first and second sides 166A and 166B of squeeze-bulb 165 are pressed inwardly (see arrows AA) which tensions the elastomeric walls and springs 180 therein (phantom view in FIG. 2A) to displace the air in the interior channel 128. FIG. 5B then shows the squeeze bulb 165 in a tensioned, compressed shape which is being urged outwardly in direction of arrows BB that thereby creates negative pressure NP in the interior channel 128. The negative pressure NP in the interior channel 128 then communicates with the interface with receiving space 150 of rolling member 120. The negative pressure NP thus provides suction forces around the rolling member 120 to communicate with a surface of a treatment site engaged by applicator tip 110 and the exposed portion of the rolling member 120. In this variation, the negative pressure in interior channel 128 is created as air is pumped outwardly through channel 172 and exit port 175 faster than air flows inwardly around the rolling member, and negative pressure is maintained in interior channel 128 after the distal tip 110 is pressed against tissue and the negative pressure mechanism 160 is further actuated during use. In another variation described below, a normally closed finger-actuated valve is provided in the distal channel portion 162 to prevent air flow around the rolling member 120 to maintain negative pressure in the interior channel 128 after actuation of the negative pressure mechanism 160.

Now turning to FIG. 7, an exploded view of the device 100 of FIG. 1 illustrates that the components of applicator body 106 can be mated and de-mated to allow for cleaning or replacement of the component parts. In a variation, the body 106 has a first proximal body portion 185 that is separable from the central body portion 186 that carries the squeeze-bulb 165 to allow cleaning of the interior thereof. The proximal portion 185 of body 106 has the function of carrying the check valve or one-way valve 170 and a flow pathway 172 to exit port 175 and can comprise one or more elements that may be separable to allow for cleaning the interior thereof. In other variations, the one-way valve 170 can consist of a flap valve, a duck-bill valve, or any form of simple elastomeric check valve. Such a one-way valve can be disposed either in the interior of the body as in FIG. 7 or the valve can be disposed at the proximal end of the device and comprise a feature of the exit port 175. As can be seen in FIG. 7. the first central body portion 186 can be de-coupled from the distal body portion 188 to allow cleaning thereof and cleaning or replacement of the roller member 120. The various components are shown in FIG. 7 with cylindrical mating features having a suitable slip fit that may be adequate to maintain negative pressure in interior channel 128 and other components of the device. In another variation, the mating connections may be provided with o-rings to enhance sealing between the components. In FIG. 7, the body portions 186 and 188 separate axially but any other form of structure can be used in a side-to-side or other arrangement to allow assembly of the members to provide the spherical receiving space 150 for receiving and capturing the rolling member 120.

FIG. 8A through 8D illustrate a method of using the device 100 of FIGS. 1, 3 and 5A-5B to treat a subject's lips 190. In FIG. 8A, the subject has topically applied flowable treatment media FM to the treatment site. It should be appreciated that the flowable or fluid media FM can consist of a liquid, gel or flowable media that can contain medications, serums, nourishing agents, botanicals, plumping agents, vitamins, colorings, cosmetics, peeling agents, desensitizers, hormones and any other flowable media known in the art for topical use. The operator of the applicator 100 then actuates the sides 166A and 166B of the squeeze bulb 165 (indicated by arrows AA) to thereby create negative pressure NP in the interior channel 128 of the device. FIG. 8B is an enlarged schematic view of the applicator tip 110 and rolling member 120 as in FIG. 8A just prior to being pressed into contact with the subject's lips 190 where the fluid media FM is shown on the tissue surface 156. In FIG. 6B, it can be seen that a negative pressure NP is provided in the interior channel 128 that communicates with the receiving space 150 around the spherical rolling member 120.

FIG. 8C illustrates a subsequent step of the method wherein the distal periphery 115 of the applicator body 106 and rolling member 120 are pressed into the tissue surface 156 and where negative pressure NP in the interior channel 128 communicates with the receiving space 150 and discontinuities 125 in the surface of the rolling member 120 to cause negative pressure NP' at the tissue surface 156. The irregularities of recessed portions 140 and projecting portions 145 in the roller surface 122 (see FIG. 3) causes the surface layer 156 of the tissue to be stretched, indented and tensioned (i.e., manipulated) as well as being exposed to negative pressure NP'. This negative pressure NP' at the tissue surface 156 can cause a transient negative pressure NP'' to migrate through the surface tissue layer 192 to a subsurface tissue region 196 which will cause upward migration of intracellular fluids towards the tissue surface 156 as indicated by arrows CC (and potentially a bruise as capillaries may be damaged). The negative pressure NP'' in subsurface tissue 196 more importantly further causes fluid media FM at the tissue surface 156 about the spherical rolling member 120 to penetrate inwardly toward the negative pressure NP''' in the subsurface tissue 196. Thus, the subsurface negative pressure NP''' causes absorbed fluid media indicated at FM' in FIG. 6C. Further, the circuitous path CP of the fluid media FM within the discontinuities 125 (see FIG. 3) of the spherical rolling member 120 causes the fluid media FM to migrate over the tissue surface 156 to maintain fluid contact with the manipulated or affected (i.e., stretched, penetrated) tissue. All of these effects cause the fluid media FM to the absorbed by, and penetrate into, subsurface tissue 196 indicated at FM'.

FIG. 8D shows the applicator tip 110, distal periphery 115 and rolling member 120 being translated across the tissue surface 156 which rolls the rolling member 120 and transiently creates negative pressure NP''' over a larger expanse of subsurface tissue 196 to cause absorption of fluid media FM' over the treated region. At the same time, small amounts of the fluid media FM'' are aspirated into the interior channel 128 in response to negative pressure NP therein.

In general, a method of the invention for treating a subject's skin or lips comprises contacting a tissue surface with a rolling member carried at a distal end of an applicator body, moving the rolling member over the tissue surface and creating negative pressure about the rolling member in contact with the tissue surface to transiently cause negative pressure in subsurface tissue to enhance permeability of the tissue surface. Typically, the treatment media is applied topically to the subject's skin or lips before use of the negative pressure applicator. During use, the translation of the applicator tip over a tissue surface causes the surface discontinuities of the rolling member to compress, stretch, tension and/or pierce the tissue surface to enhance penetration or absorption of the treatment media.

As a negative pressure in the interior channel 128 of the device is reduced during use, the operator can intermittently or continuously actuate the squeeze bulb 165 to increase or maintain negative pressure NP in the interior channel 128 while translating the applicator tip 110 and rolling member 120 across the tissue surface 156. All of these effects combine to enhance fluid absorption and penetration. Following use, the operator can disassemble the device 100 as shown in the exploded view of FIG. 7 and clean the interior channel 128 and other components for example with running water. The device components then may be reassembled for future use.

The variation of FIGS. 1, 3, 5A and 5B illustrate the squeeze bulb 165 as a form of pump that is suitable for creating negative pressure in interior channel 128 of the applicator 100, but it should be appreciated that any type of manually actuated pump may be used and fall within the scope of the invention. Typically, a positive displacement pump is suitable which can be a piston pump, a syringe pump, bellows pumps, a peristaltic pump, a gear pump, an impeller pump, a vane pump or a diaphragm pump.

FIG. 9 illustrates a distal applicator tip 205 of another variation of an applicator that is otherwise similar to that of FIGS. 1 and 3. In FIG. 9, the rolling member 120' is similar to that of FIG. 3 with similar projecting portions 145. In this variation, the recessed portions 140' have an abrasive surface 210 which, for example, can be diamond dust adhered thereto or sharp abrasive edges molded into a plastic rolling member. The abrasive surface 210 provides for traction between the rolling member 120' and the skin surface 156 as well causing micro-penetrations into the skin surface 156 as a form of tissue manipulation to thereby enhance penetration of fluid treatment media into the skin as described previously. In this variation, the distal periphery 115' is shown to extend distally compared to that of FIG. 3 such that the surface 122' of the rolling member 120' does not extend beyond the distal periphery 115'. In such an embodiment, where the rolling member surface 122' is somewhat recessed in the tip 205, it is useful to provide increased traction between the rolling member 120' and a skin surface. As can be understood in FIG. 9, the abrasive surface 210 is recessed relative to the outermost surfaces of the projecting portions 145 so that the rolling member 120' rolls smoothly in the receiving space 150.

FIG. 10 illustrates another variation of distal applicator tip 215 that is similar to previous embodiments except the rolling member 220 has projecting portions 225 surrounded by a recessed region 240 that carries a plurality of sharp elements that can be micro-needles 244 or molded sharp points that provide for traction between the rolling member 220 and the tissue surface 156 as well for penetrating the skin surface 156 as a form of tissue manipulation to thereby enhance penetration of fluid media into the skin. In FIG. 10, a limited number of micro-needles 244 are shown, but the number may range from dozens to many hundreds of such micro-needles. In the variation of FIG. 10, the distal peripheral element 255 that surrounds the exposed portion of the rolling member 220 is shown of a resilient elastomeric material with an annular void 256 therein to allow the element is to be flexed and compressed when in contact with tissue to create an effective seal. The distal end 258 of the housing is configured to prevent the peripheral element 255 from being flexed into contact with the rolling member 220.

Figure 11:
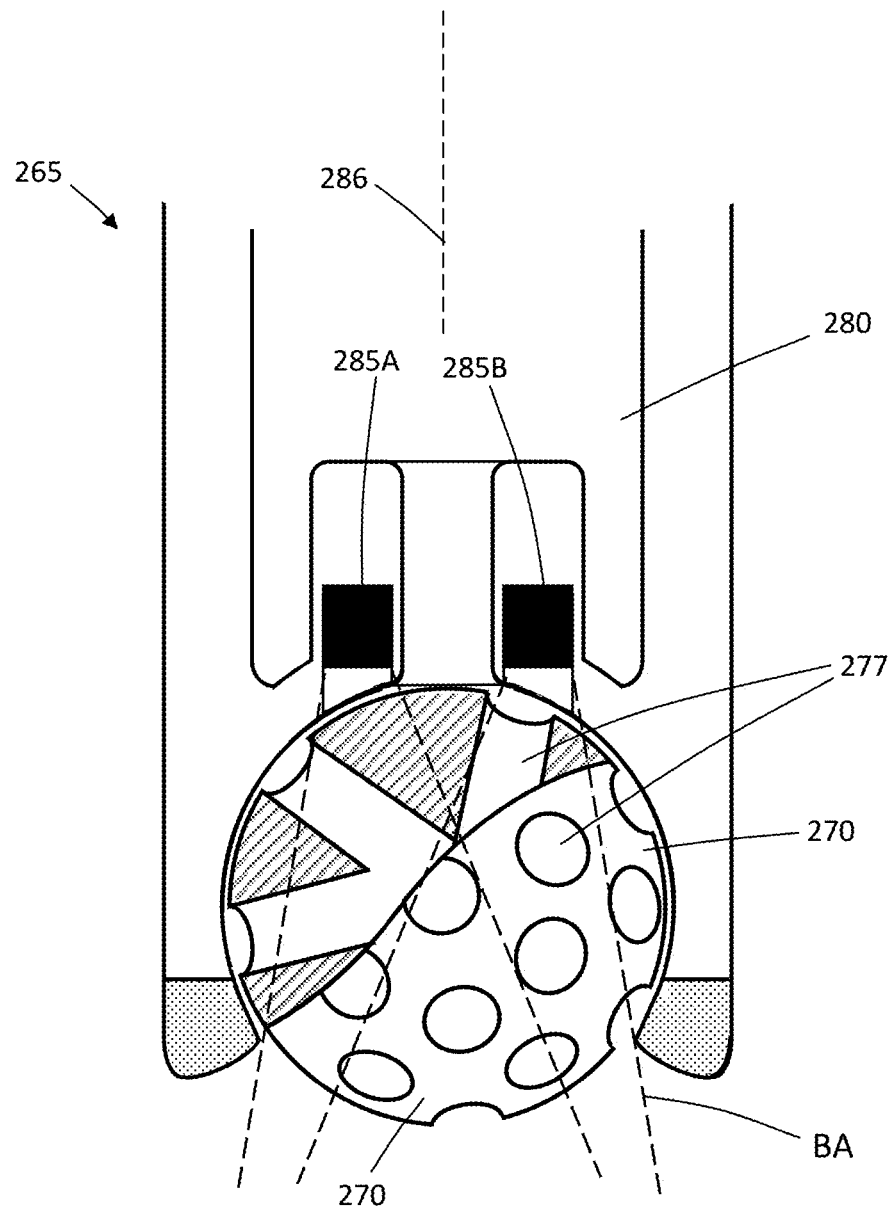
FIG. 11 is a cut-away view of another variation of applicator tip similar to that of FIG. 1 where the distal housing carries LEDs for applying light energy to tissue.

FIG. 11 illustrates another variation of distal applicator tip 265 that has a rolling member 270 with outer surface portion 275 and through-channels or bores 277 that function as means for communicating a negative pressure NP in interior channel 280 with tissue in contact with the rolling member 270. The number of bores 277 can range in number from 10 to 100 or more and can be any suitable dimension ranging from 1% of the diameter of the rolling member to 20% of the diameter or rolling member 270. FIG. 11 also illustrates another feature in this variation of applicator tip 265 that comprises at least one LED and in this variation is shown as two LEDs 285A and 285B that emit at least one wavelength of light for treating tissue. In this variation, the rolling member is formed of a transparent material such as a plastic or glass to permit light transmission therethrough. The LED beam angle BA is shown in FIG. 11 and can range from 15° to 60°. In a variation (not shown), the rolling member 270 can carry embedded or surface light shaping diffusers that comprise micro-structures randomly or controllably positioned on or within the rolling member 270 to modify the LED light beam by changing the direction of its energy. Such light shaping diffusers can shape the light beam(s) to propagate laterally relative to the axis 286 of the applicator tip 265 to broadly treat tissue in contact with the rolling member 270. In the variation of FIG. 11, the LEDs 285A and 285B can emit a red-light wavelength which research indicates can penetrate deep into skin and stimulate the mitochondria, which has an anti-inflammatory and rejuvenating effect. Such red-light therapy has been found to accelerates skin repair, regulate oil production and improve circulation, and is known as a medically approved treatment for rosacea. The LEDs also can emit blue light which has antibacterial properties for the treatment of acne, eczema, and psoriasis. Other wavelengths also can be used and fall within the scope of the invention. The LEDs 285A and 285B can be coupled to a re-chargeable battery (not shown) carried by the applicator.

Figure 12:
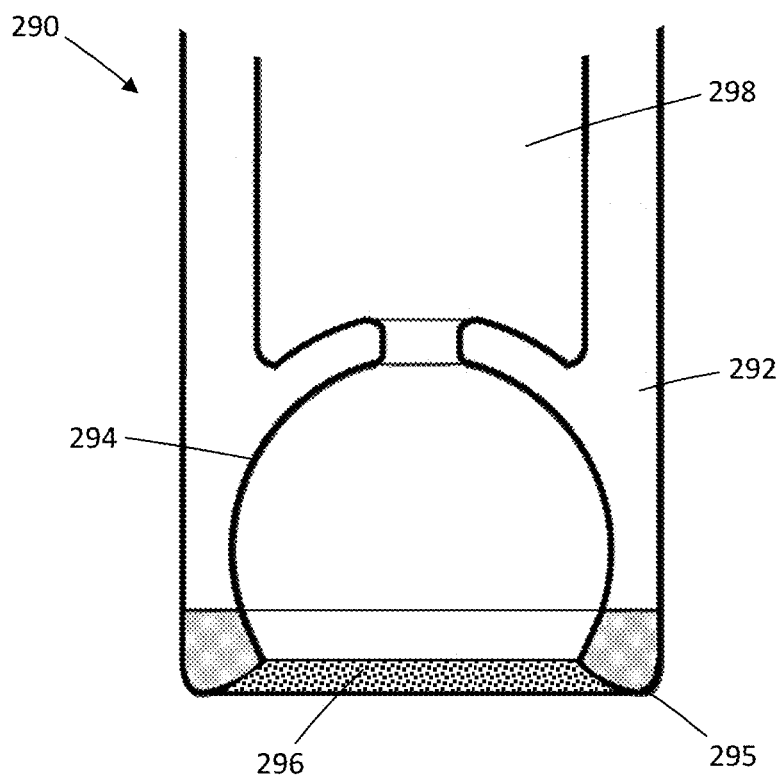
FIG. 12 is a sectional view of another variation of roller housing that is configured with an abrasive surface around a distal periphery of the applicator body for providing a dermabrasion effect to enhance fluid penetration into a skin surface.

FIG. 12 illustrates a variation of an applicator body 290 with a distal housing portion 292 with a receiving space 294 for receiving a rolling member (not shown), where the rolling member can be similar to any previously described embodiments. In this variation, the distal periphery 295 is configured with a portion having an abrasive surface 296 that can consist of abrasive particles such as diamond dust adhered to the distal periphery 295. Alternatively, the abrasive surface 296 can consist of sharp edges and features formed in a molded, machined, printed or etched material that comprises the distal periphery 295. The abrasive surface 296 functions to abrade and remove a skin surface layer as the distal housing 292 and periphery 295 is translated over a tissue surface. Such an abrasive effect enhances fluid penetration into and through the surface tissue layer. In all other aspects, the rolling member and negative pressure in the interior channel function 298 as described previously to perform methods of the invention.

Figure 13:
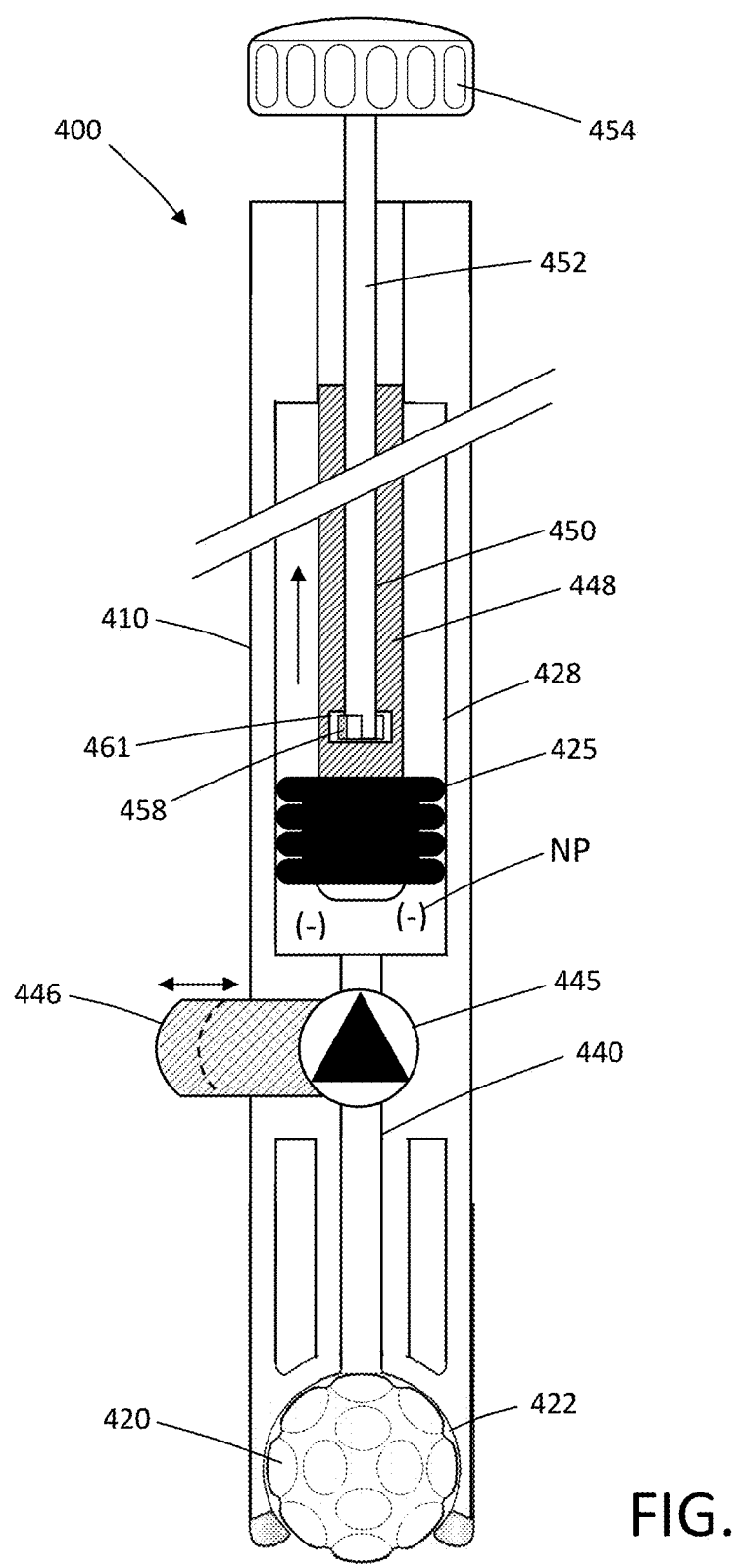
FIG. 13 is a sectional view of another variation of a negative pressure treatment device where negative pressure is created by a syringe-type piston mechanism, and where the applicator further includes a finger-actuated valve for releasing aspiration forces to treat tissue.

FIG. 13 illustrates another variation of a treatment device 400 that is similar to that of FIGS. 1, 3 and 4 except that a different negative pressure mechanism 405 is provided in the applicator body 410. In the variation of FIG. 13, the rolling member 420 and the receiving space 422 are the same as described previously. The variation of FIG. 13 is adapted to create negative pressure NP with a syringe-type piston 425 that is movable in an interior syringe chamber 428 to provide negative pressure NP therein. The manually actuated piston 425 and chamber 428 communicate with a flow channel 440 that interfaces with rolling member 420 as described previously. In this variation, a finger-actuated valve 445 with actuator button 446 that has a normally closed position is provided in the flow channel 440 intermediate the syringe chamber 428 and the rolling member 420. In use, the negative pressure NP can be maintained in the syringe chamber 428 until the operator actuates the valve 445 apply negative pressure or suction forces to an engaged tissue surface. In one variation, the piston 425 is coupled to an actuator shaft 448 that is moved axially in the proximal direction to create negative pressure NP in the syringe chamber 428. The actuator shaft 448 is shown in FIG. 13 as a tubular member with a bore 450 therein that receives a telescoping member 452 with grip 454. The telescoping member 452 has distal tabs 458 that can be rotated in an offset 461 in bore 450 to engage and disengage the shaft 448 to thus provide an axially collapsible shaft assembly.

Figure 14:
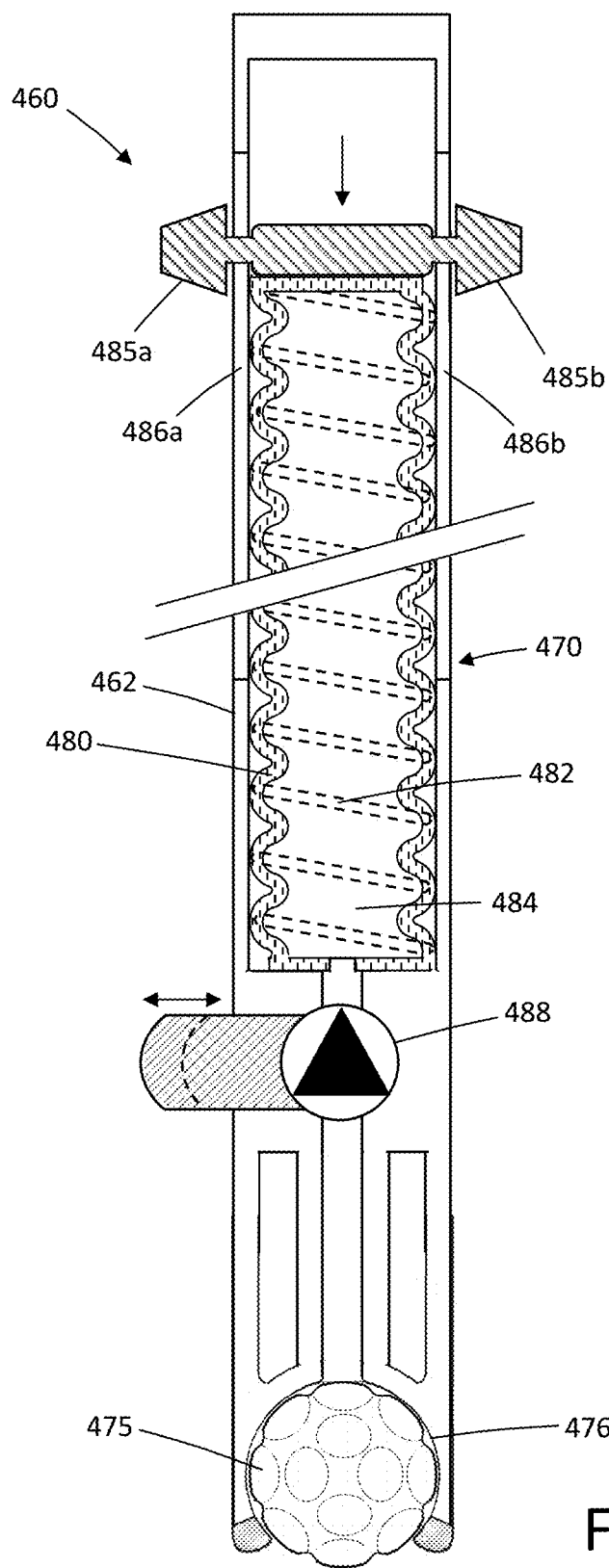
FIG. 14 is a sectional view of yet another variation of a negative pressure treatment device where negative pressure is created by a manually-actuated bladder or bellow mechanism.

FIG. 14 illustrates another variation of a treatment device 460 with an applicator body 462 that is similar the previous embodiment of FIG. 13 except that it provides a different negative pressure mechanism 470. In the variation of FIG. 14, the rolling member 475 and receiving space 476 are the same as described above. In the variation of FIG. 14, negative pressure is provided by a bladder or bellows 480 that is urged toward an expanded shape by a strong helical spring 482 to create negative pressure in an interior chamber 484 thereof. The bladder 480 is collapsible by finger-actuated tabs 485a and 485b that extend through slots 486a and 486b in the applicator body 462. A finger-actuated valve 488 is provided as in the previous embodiment, where the valve is held in an open position as the bladder 480 is actuated to the collapsed position. In all other aspects, the method of using the device 250 of FIG. 8 is the same as described above.

Figures 15, 16:
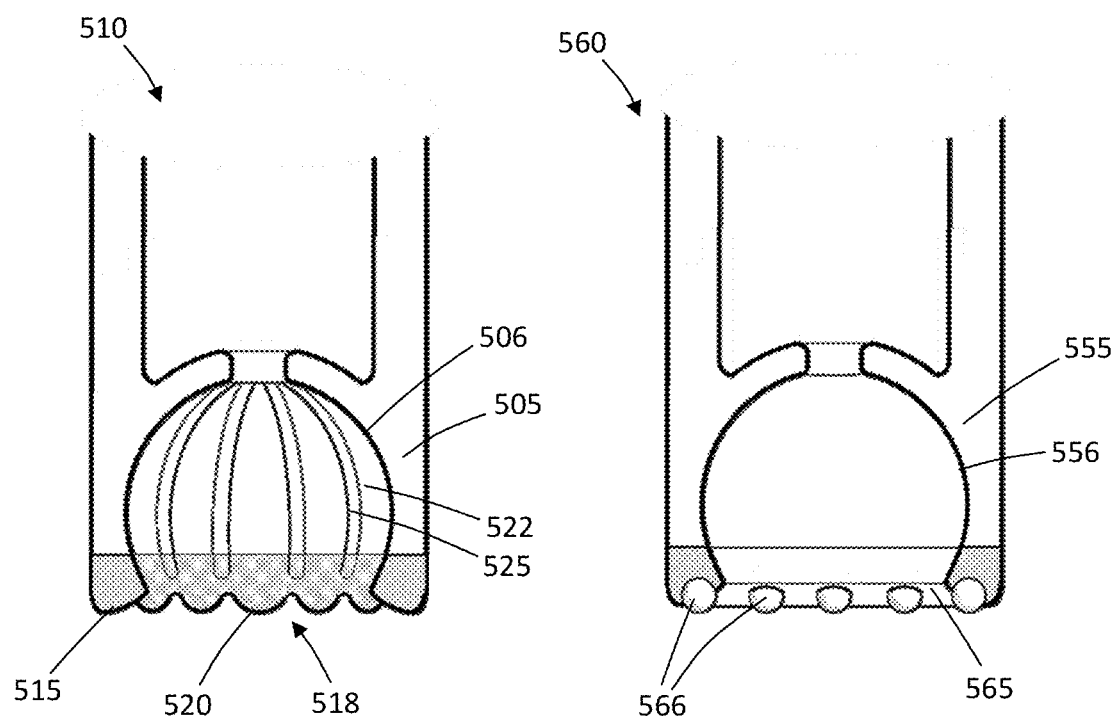
FIG. 15 is a sectional view of another variation of roller housing that is configured with an undulating distal periphery for manipulating tissue.
FIG. 16 is a sectional view of another distal roller housing that is configured with a distal periphery carrying a plurality of rollers for reducing friction with a tissue surface during use and for manipulating tissue.

FIG. 15 illustrates another variation of a distal housing 505 and receiving space 506 of an applicator body 510 shown without a rolling member, where the rolling member can be similar to the previous embodiment of FIGS. 1 and 3 or other embodiments. In this variation, the distal periphery 515 is formed with a series of undulations 518 that are adapted to manipulate a tissue surface similar to the irregular surface of a rolling member. Thus, as the distal housing 505 is translated over a tissue surface, the projecting portions 520 of the undulations will indent, tension, and stretch surface tissue which can enhance fluid penetration into and through the surface tissue layer. FIG. 15 also shows that the spherical inner surface 522 of the roller receiving space 506 has surface discontinuities or grooves 525 therein that provide a flow path for negative pressure NP in channel around the rolling member. Thus, there can features in either or both the surface of the rolling member and the surface of the receiving space 522 that provide flow pathways for negative pressure NP to perform the method of the invention. In this variation, it should be a appreciated that a rolling member (not shown) could have an entirely spherical abrasive surface and rotate smoothly in the receiving space 506 since the number of apices of abrasive elements would number in the thousands and the flow pathway for negative pressure to the tissue surface would be provide largely or entirely by the surface discontinuities or grooves 525 and partly by the interstices between the projecting portions of the abrasive elements.

FIG. 16 illustrates another variation of a distal housing 555 and receiving space 556 of an applicator body 560 where the distal periphery 565 of the housing 555 carries a plurality of roller balls 566 which project slightly from the distal periphery 565. Such roller balls 566 can serve the function of manipulating tissue as described above while the same time reducing friction of the distal housing 555 with the tissue surface as it is translated over a tissue surface.

Figure 17:
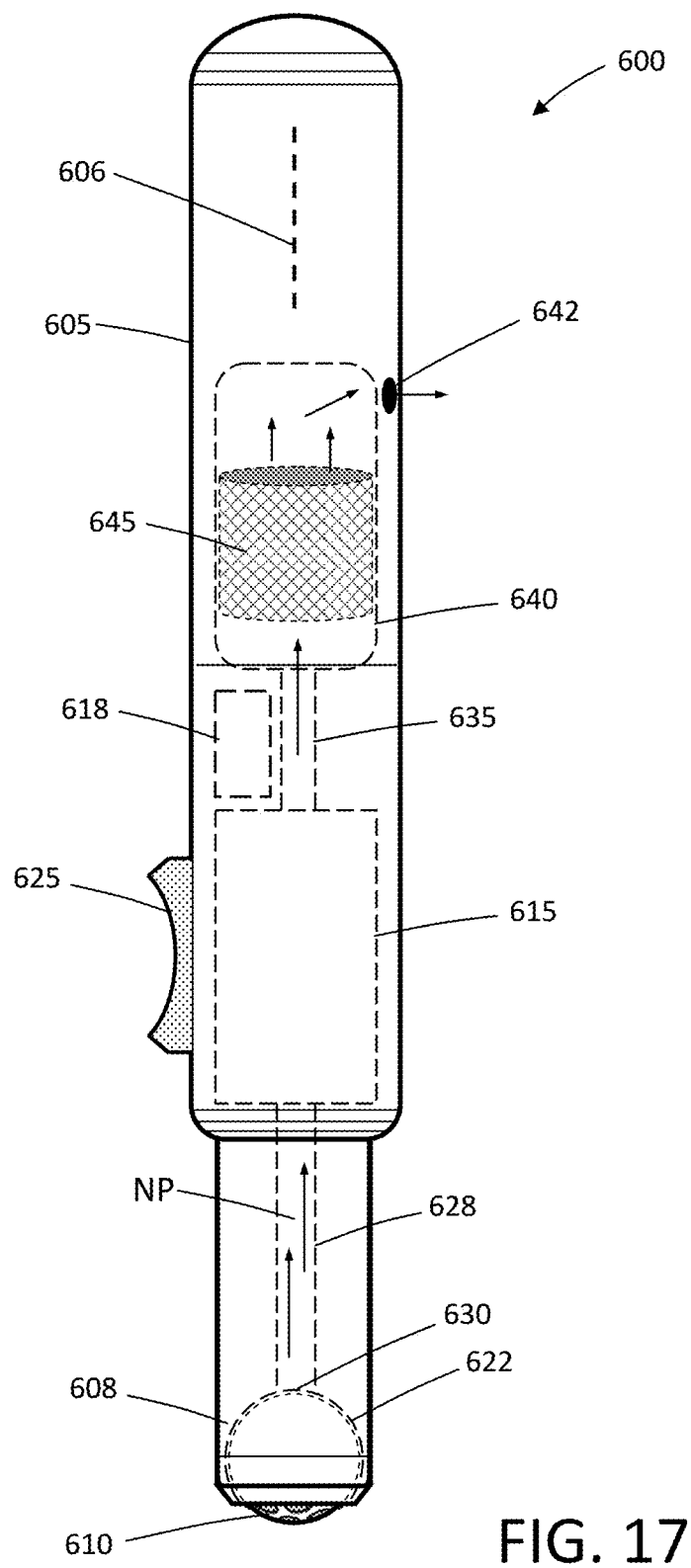
FIG. 17 is an elevational view of another variation of skin treatment device or applicator with a distal rolling member and a DC motor driven pump assembly with filter carried in the applicator body.

FIG. 17 illustrates another variation of a treatment device 600 that is similar to that of FIGS. 1, 3 and 4 with an elongate body 605 extending about longitudinal axis 606 and is configured with a distal housing 608 that carries a rolling member 610. In this variation, the negative pressure mechanism comprises a pump assembly 615 that comprises a pump and DC motor powered by a battery 618, both of which are carried in the applicator body 605. This variation again is adapted for use with a topically applied treatment media as described previously. In the variation of FIG. 17, the rolling member 610 is rotatable in any direction in the receiving space 622 of the distal housing 608 and is similar to previous variations. The pump assembly 615 can comprise any suitable form of pump, and in a variation is a diaphragm pump coupled to a 3.7 W DC motor that is operated by rocker switch 625 in the applicator body 605. In one variation, the rocker switch 625 is adapted to select between one or more settings of negative pressure, for example, up to 63 kPa (9.14 psi). The variation of FIG. 17 is adapted to create negative pressure NP in the distal aspiration or extraction channel 628 that interfaces with rolling member 610 about an open termination 630 of the said aspiration channel 628. Thus, the pump assembly 615 aspirates air and fluid droplets through or around the rolling member 610 and through the pump assembly 615 into the proximal aspiration or extraction channel 635, which can include an interior chamber 640, in the applicator body 605. At least one vent or aperture 642 is provided for exhausting flow media air from extraction channel 635 and chamber 640. As can be seen in FIG. 17, the interior chamber 640 carries a filter 645 for capturing liquid droplets of the aspirated treatment media. In all other aspects, the variation of FIG. 17 functions as previous variations to enhance fluid penetration into a subject's skin, and the rolling member 610 can consist of any of the various types described above. While this variation shows that pump assembly 615 is powered by a battery 618, it should be appreciated that a power cord and a remote power source also fall within the scope of the invention. Further, in the variation shown in FIG. 17 that uses a battery 618, the applicator body 605 can be configured with electrical contacts in a surface of the body 605 to cooperate with a charging stand as is commonly known in the field of battery-operated handheld devices. As in previous variations, the applicator body 605 can consist of several mating components that can be disassembled to allow cleaning of the interior components of the device including the rolling member 610, the receiving space 622, the pump assembly 615, the distal aspiration channel 628, the proximal aspiration channel 635, chamber 640 and the filter 645.

Figure 18:
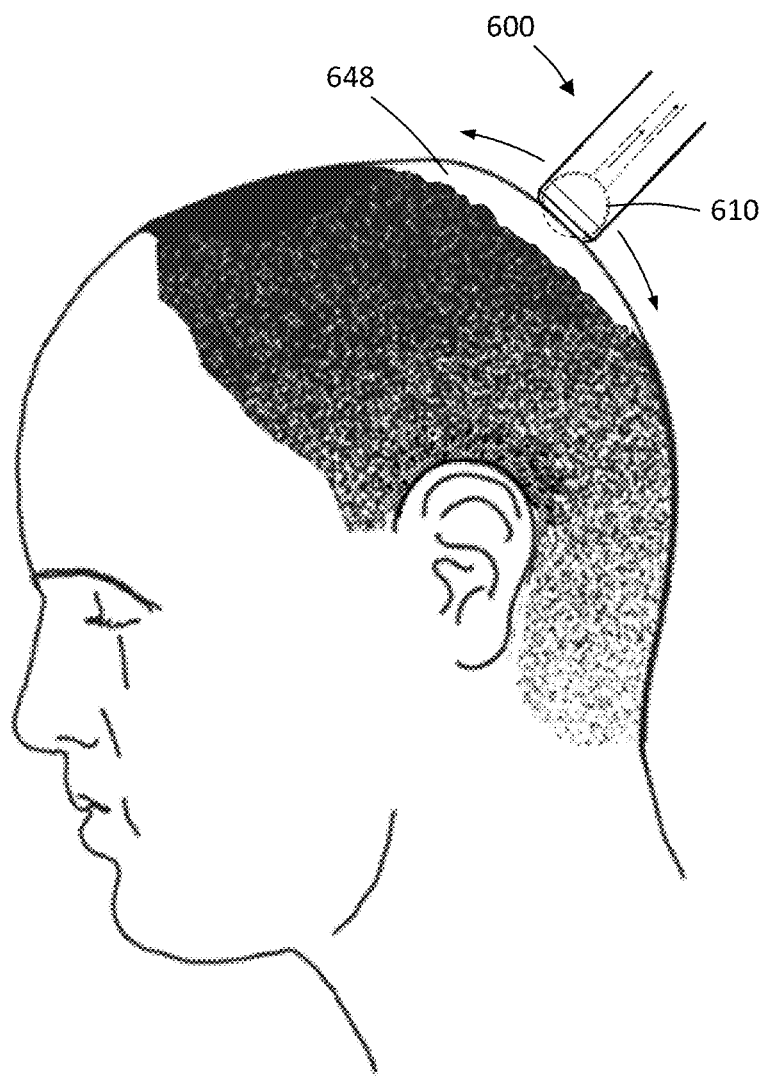
FIG. 18 is an illustration of a method of treating hair loss using the applicator of FIG. 17 to apply and deliver pharmacologic agents to a treatment site on a patient's scalp.
Figure 21:
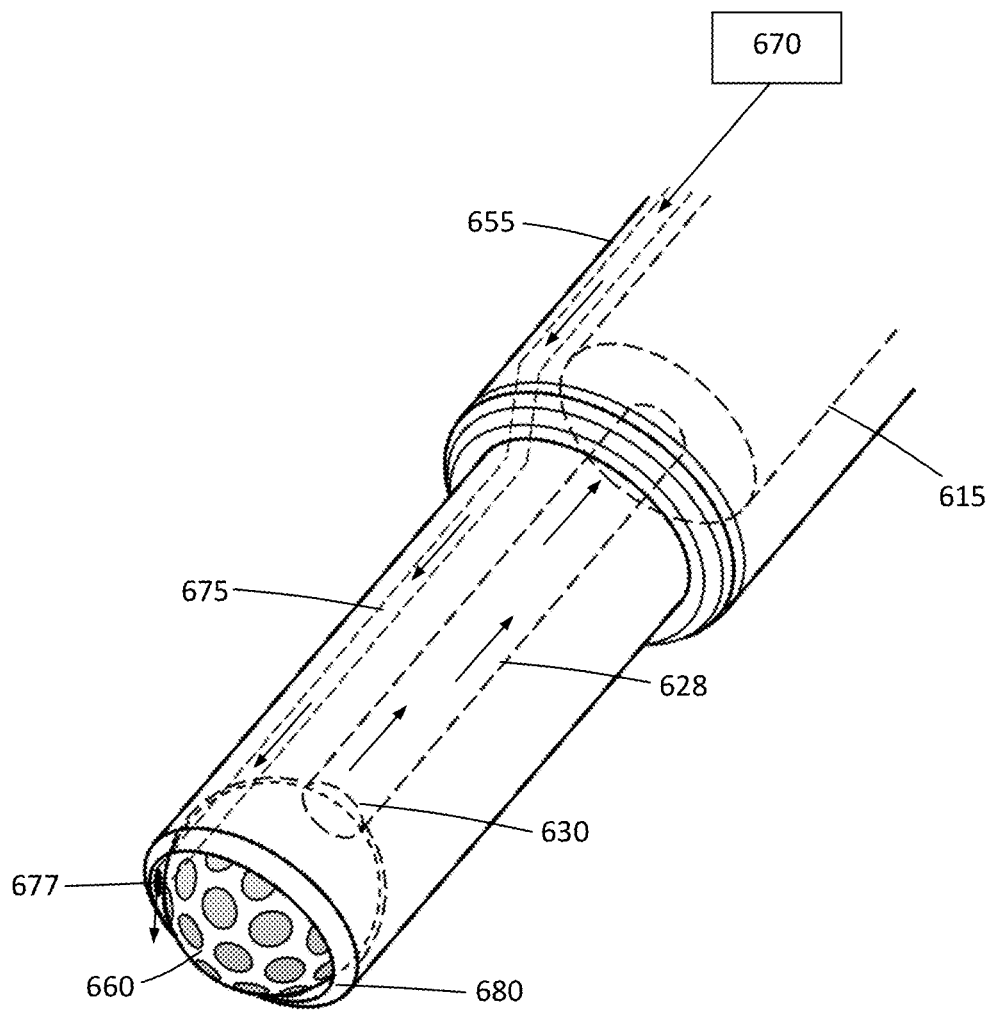
FIG. 21 is an enlarged perspective view of the distal portion of the applicator of FIG. 19.

The device of FIG. 17 is adapted for use in the methods of delivering or applying fluid to tissue as described previously. In another method, the applicator 600 of FIG. 17 can be used to treat hair loss as shown in FIG. 18. It can be appreciated that the applicators described above, including that the applicator of FIG. 17, include an internal pump assembly 615 and are designed to enhance penetration of fluid treatment media into subsurface tissue under a targeted site of the subject's skin. In FIG. 18, the applicator or treatment device 600 is shown being used to apply and enhance the penetration of treatment media into the skin of a subject's scalp 648. In this method, the treatment media can include at least one of finasteride, minoxidil, dutasteride and a corticosteroid. Currently, such pharmacologic agents have been applied topically and have shown to have an effect in the restoration of hair growth. The applicator 600 of FIG. 17 and the applicator 650 shown in FIGS. 19-21 are thus adapted to enhance the penetration of such agents into subsurface tissue below the skin surface to enhance hair growth. In other variations, the treatment media can include a psoralen and the applicator body can include LEDs with the appropriate wavelength to interact with the psoralen to stimulate hair growth. Currently, psoralens have been investigated for enhancing hair growth when irradiated with selected light wavelengths, for example UV wavelengths.

In general, a method for treating a subject's hair loss comprises topically applying a hair growth treatment media to targeted tissue of a subject, contacting the tissue and treatment media with an applicator, and causing negative pressure about the applicator in contact with the tissue to transiently cause negative pressure in subsurface tissue to enhance penetration of the treatment media into the subsurface tissue. Further, the method can move the applicator over the tissue to treat broad areas of the subject's scalp. In such a treatment, the treatment media includes at least one finasteride, minoxidil, dutasteride, a corticosteroid and a psoralen. The step of causing negative pressure includes actuating a vacuum pump mechanism in the applicator body, or alternatively, the negative pressure source is remote form the applicator and coupled to the applicator with a flexible tubing. In one variation, the negative pressure is pulsed to allow manipulation and relaxation of the tissue surface to enhance fluid penetration. In another variation similar to previous applicators, the negative pressure is provided at the interface of the subject's skin by a rolling member 610 in the applicator tip which provides a flow path through and/or around the rolling member 610 (see FIG. 17). As described in previous variations, moving the rolling member 610 manipulates tissue to thereby enhance penetration of the treatment media into subsurface tissue. Such tissue manipulation can consist of compressing, stretching, tensioning and/or piercing the tissue surface using the surface features of the rolling member 610. In a variation, the rolling member 610 further removes or exfoliates the epidermis with surface features of the rolling member to thereby enhance penetration of the treatment media in the targeted tissue. The applicator body of FIG. 17 can further be provided with the source of treatment media in a cartridge or reservoir carried by the applicator body as will described next in the variation of FIGS. 19-21. The method of treating hair loss described above also can be performed with any of the treatment devices of FIGS. 22-29 that provide negative pressure and tissue manipulation as well as the treatment device of FIGS. 29-30 that provides negative pressure and manipulates tissue without a rolling member.

Figure 23:
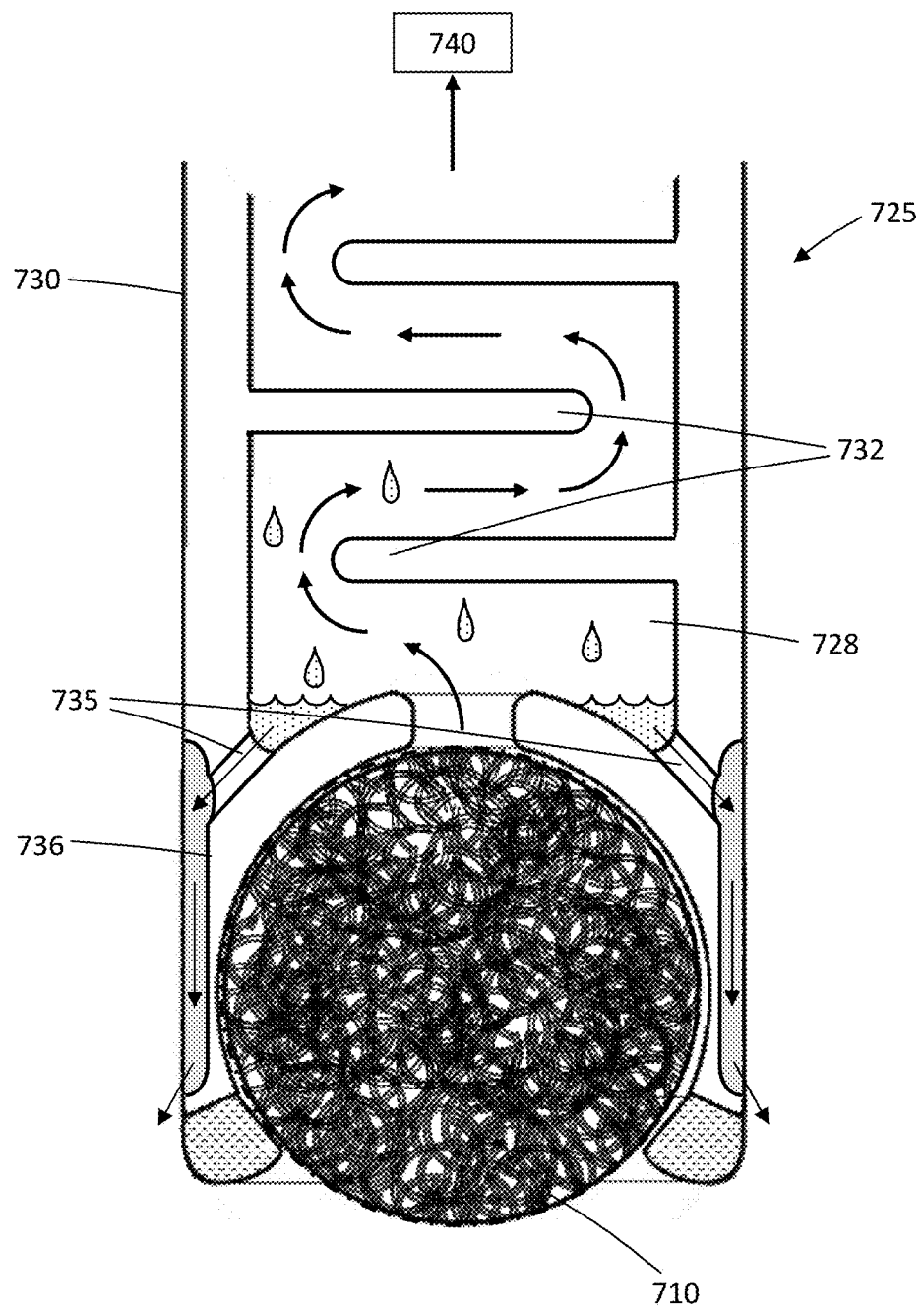
FIG. 23 is a section view of a distal portion of another variation of an applicator that includes baffles in an outflow channel to capture liquid droplets from outflows.

Now turning to FIG. 19-21, another variation of applicator 650 is shown that includes an elongated applicator body 655 with a distal rolling member 660 as described previously. In this variation, the applicator body 655 again carries a pump assembly 615 and battery 618 operated by a switch 625 with fluid and water droplets being extracted through the distal channel 628 and pump assembly 615 to a proximal chamber 640 carrying a filter 645 as described previously. In the embodiment of FIG. 19, the applicator 655 carries a fluid reservoir 670 that may be detachable or non-detachable and is adapted to carry the treatment fluid TF. FIG. 19 shows the applicator body 655 with the various components in phantom view and FIG. 20 shows the treatment fluid reservoir 670 in a cartridge 672 removed from the applicator body 655. In this variation, at least one fluid inflow channel 675 is provided from the fluid reservoir 670 to the distal end 676 of the applicator body 655. In a typical variation, the open termination 677 of the fluid inflow channel 675 with the proximate to the surface of the rolling member 660 but in should be appreciated that the distal edges of the applicator body 655 may form a seal on the subject's skin as described previously. In another variation, the open termination 677 of the at least one fluid inflow channel 675 can be in an exterior surface of the applicator to allow fluid to be applied to the skin outwardly of the rolling member 660, which is similar to that as shown in FIG. 23 which is further described below. In FIGS. 19 and 21, a single fluid inflow channel 675 is shown but it can be appreciated that a plurality of such channels can be provided with open terminations in the distal end of the applicator.

A key feature of the device of FIGS. 19-21 is the configuration of the components that allows for actuation of the negative pressure source to draw fluid from the cartridge or reservoir 670 through the at least one inflow channel 675 only when the distal tip of the applicator and the rolling member 660 are engaged with the subject's skin. It can be understood that when the distal tip 680 of the applicator body 655 is not in contact with tissue and with the pump assembly 615 being actuated, the only effect will be to pull air around or through the rolling member 660 and into the extraction channel 628 and the interior chamber 640 of the applicator. However, when the distal tip 680 of the applicator is sealed against the subject's tissue surface, then actuation of the pump assembly 615 will apply suction to the distal opening 677 of the fluid inflow channel 675 to draw fluid from the fluid reservoir 670 into the distal tip 680 of the applicator.

Figure 22:
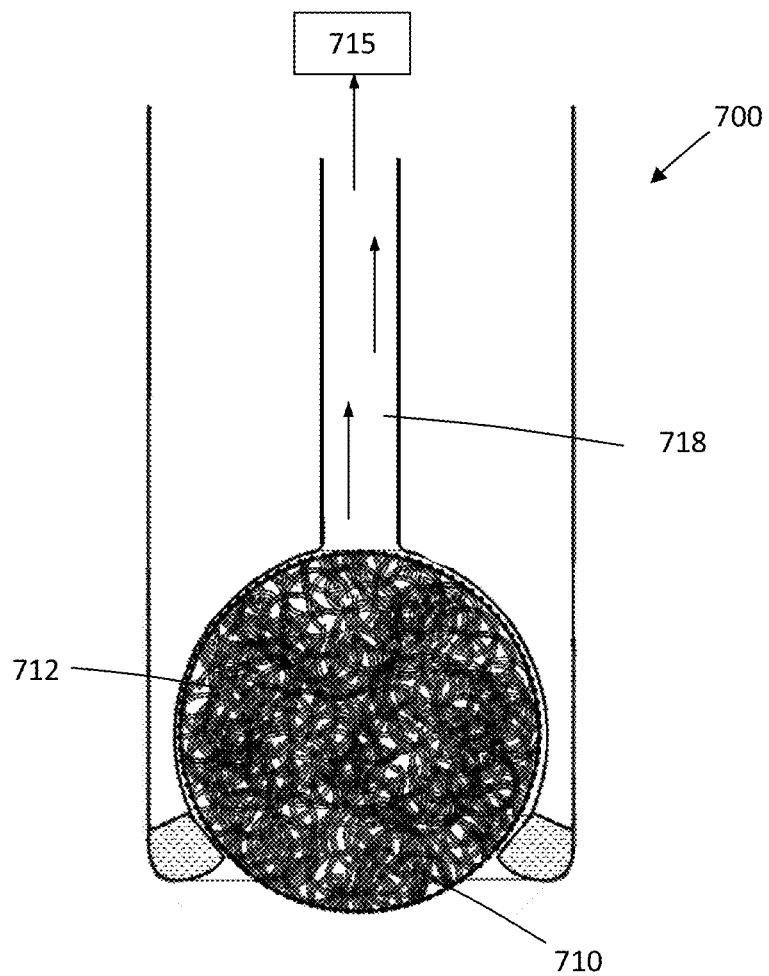
FIG. 22 is an enlarged sectional view a distal portion of another applicator where a spherical rolling member comprises a mesh structure that functions to manipulate tissue as well as functioning as a filter.

FIG. 22 illustrates another variation of working end 700 of an applicator 705 that is similar to previous embodiments except for the rolling member 710 comprises a ball or sphere of a mesh fabricated of fine metal wires, polymer filaments or a combination thereof indicated at 712 that are formed into a spherical shape. The spherical shape can optionally be maintained by adhesives or other suitable means to create a porous spherical member 710. Such a porous spherical member 710 can provide for multiple functions, including comprising a structure with an abrasive surface that can exfoliate skin, providing irregularities in the surface of the rolling member 710 for manipulating tissue and acting as a filter as the negative pressure source 715 suctions treatment fluid through the working end 700 to through outflow channel 718 as shown in FIG. 22. When the mesh rolling member 710 interfaces with a smaller diameter outflow channel 781, it can be appreciated that fluid droplets will be aspirated more readily in a direct path through the rolling member 710 and some liquid will be trapped in interstices of the mesh and fall back onto the skin surface. In other words, such a rolling member 710 can function as a filter and limit the volume of liquid droplets aspirated through the applicator 700. This in turn, can result in a greater volume of treatment media on the skin surface for penetrating the skin by action of the rolling member 710. In a variation, the surfaces of the filaments that make up the rolling member 710 can have a hydrophobic or ultrahydrophobic coating for causing fluid to migrate outwardly or distally under the effect of gravity back onto the tissue surface. In other variations, a combination of hydrophilic and hydrophobic surfaces of the materials of the mesh rolling member 710 can be used to trap and filter liquid droplets from the aspirated media.

FIG. 23 is another variation of applicator working end 725 that similar to that of FIG. 22 with a mesh rolling member 710. In this variation, the extraction channel 728 in the interior of the applicator body 730 includes fluid trapping features 732 for capturing liquid droplets that are aspirated through or around the rolling member 710. The trapping features comprise baffles that extend from opposing sides of the extraction channel 728 or can comprise annular element with non-aligned apertures therein. Such features can have angled surfaces to cause captured fluid droplets to migrate distally under gravity. In the variation of FIG. 23, the captured liquid can enter drain channels 735 that extend to the exterior surface 736 of the applicator body 730 where the liquid can exit the applicator and fall back onto the patient's skin. In a variation, the drain channels 735 can include one-way valves (not shown) such as a sensitive silicone flap valve to allow the weight of the captured fluid to be released through the channels 735, such that the negative pressure source 740 does not affect the one-way valves.

Figure 24:
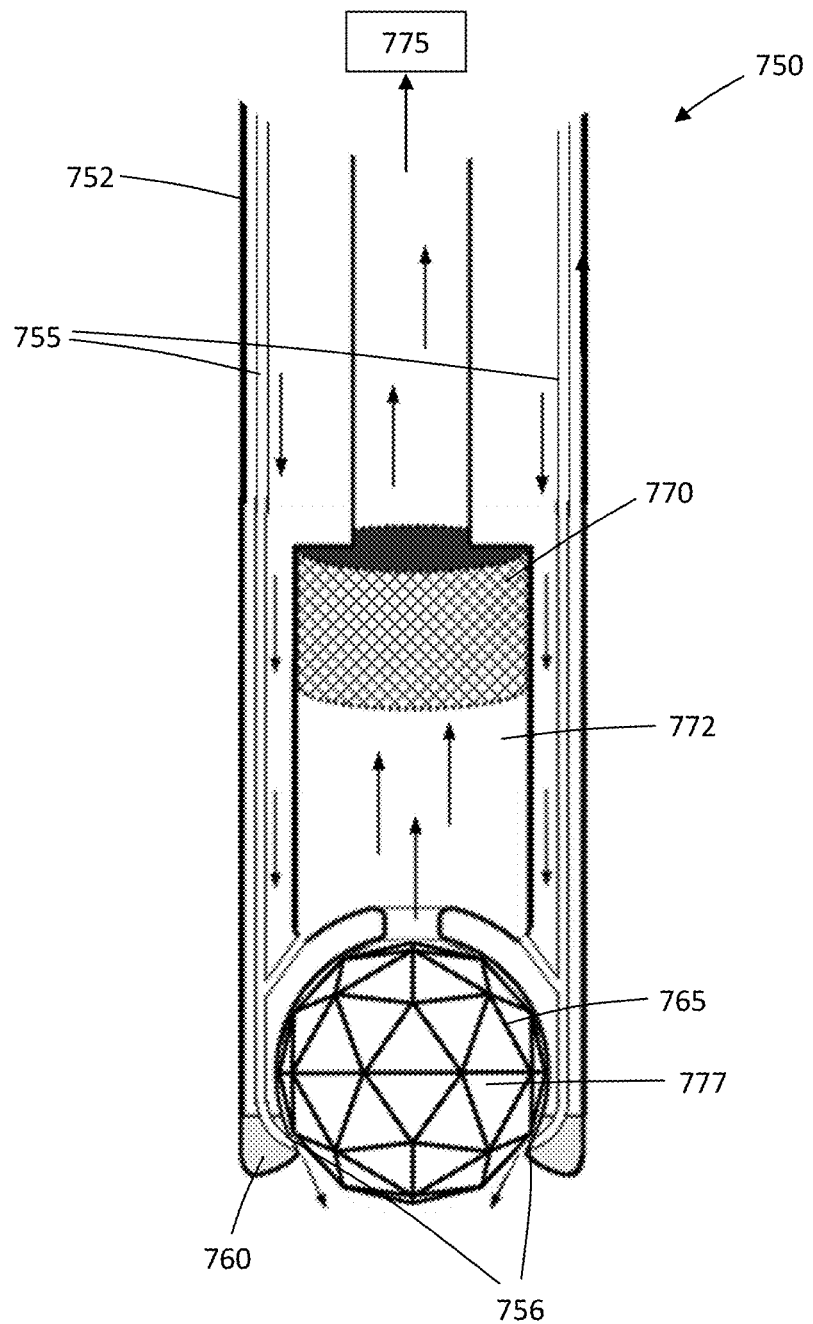
FIG. 24 is a sectional view of the distal portion of another variation of an applicator that carries a faceted rolling member, where the applicator body has fluid inflow channels.
Figure 25:
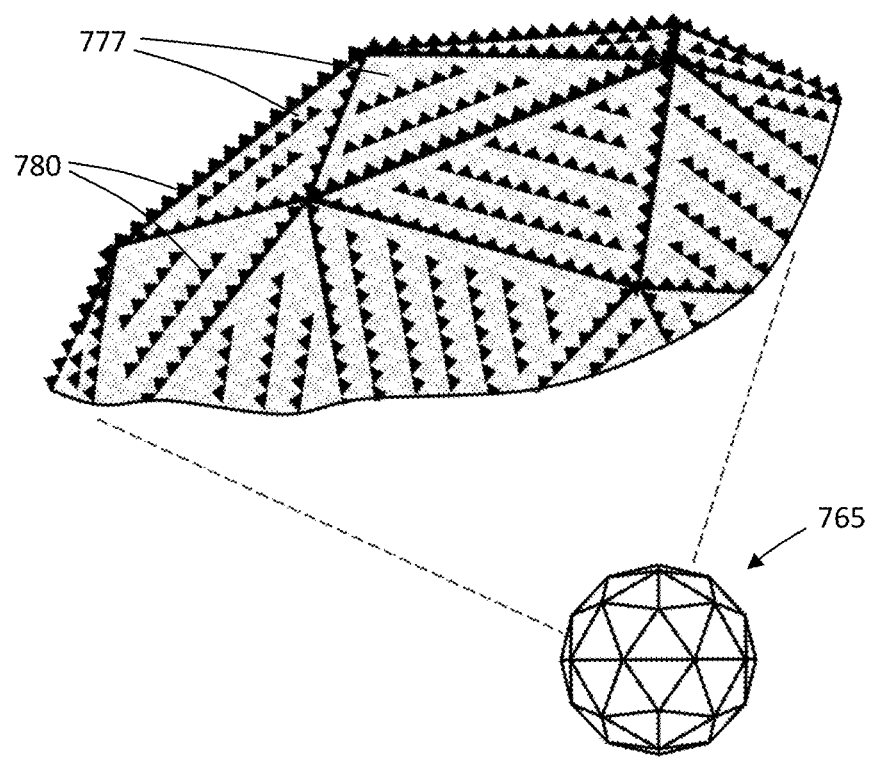
FIG. 25 is an enlarged view of a fragment of the faceted rolling member of FIG. 24 showing diamond particles adhered to the rolling member.

FIG. 24 illustrates another working end 750 of an applicator body 752 that is similar to that of FIGS. 19-21 where the system carries a fluid cartridge and fluid flows are drawn from a fluid cartridge to the inflow channels 755 to open terminations 756 in the distalmost tip 760 of the applicator around the rolling member 765. This variation of working end 750 includes a filter 770 in the extraction channel 772 distal to the pump assembly 775. FIG. 24 further shows a rolling member 765 with facets 777 which is again adapted for rolling over tissue and manipulating tissue. In the enlarged view of a fragment of the rolling member 765 of FIG. 25, it can be seen that the surface of the rolling member 765 is configured with facets 777 that have micro-penetrating elements that can comprise rough or course diamond particles 780. In this variation, the rolling member 765 rolls over tissue and caused micro-penetrations in the tissue surface caused by the manually applied pressure of the rolling member 765 against tissue in combination with aspiration forces about the facets 777 of the rolling member 765 to enhance penetration of fluid media into subsurface tissues.

Figure 26:
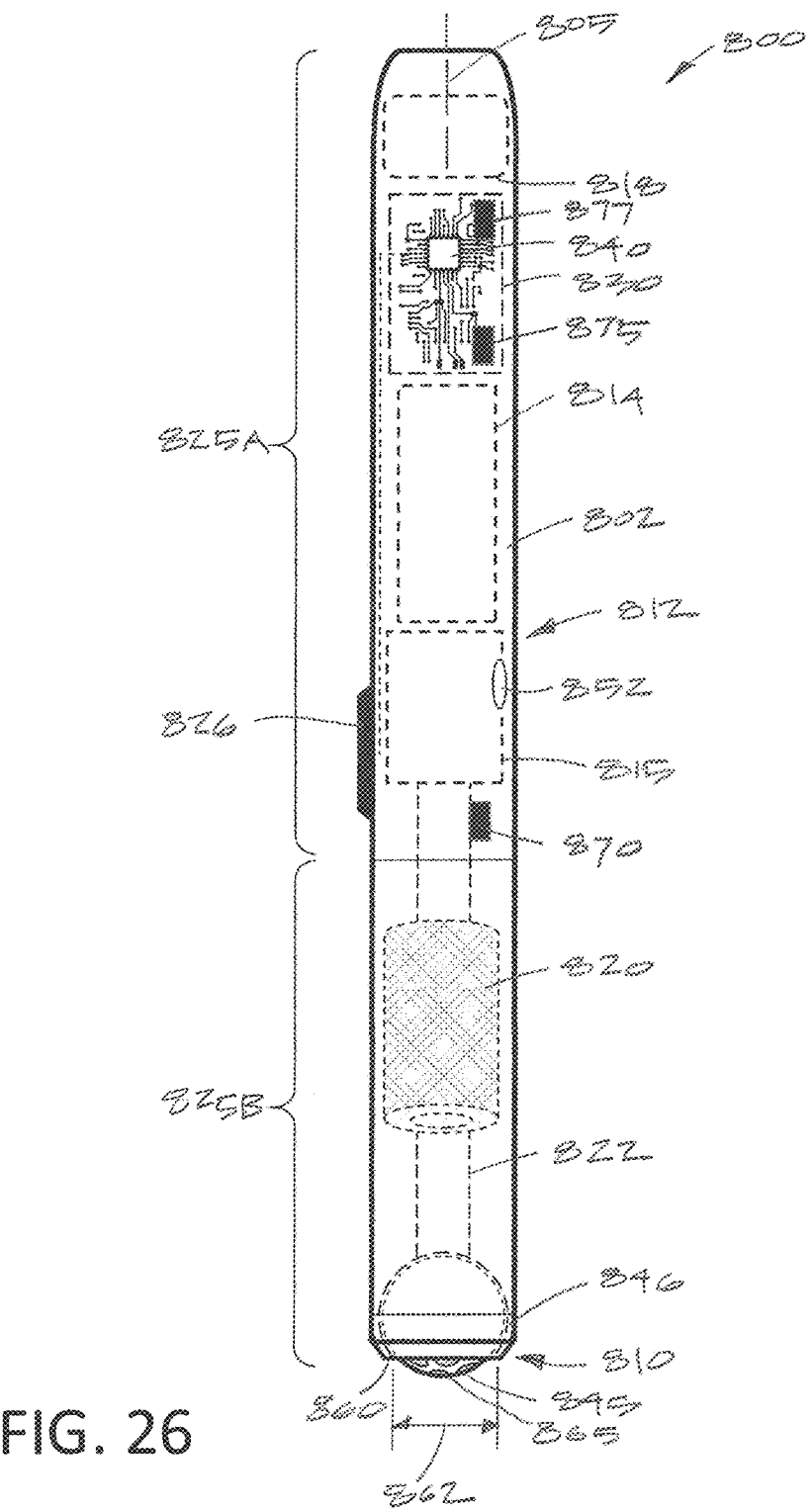
FIG. 26 is a transparent elevational view of another variation of applicator that carries a distal rolling member, a DC motor driven pump assembly, a filter and a battery.

Now turning to FIG. 26, another variation of a lip or skin treatment device is shown which again comprises a self-contained elongated hand-held applicator 800 with an applicator body 802 that extends about a central axis 805 to a distal tip 810 adapted for contacting and treating targeted tissue. The applicator 800 carries a pump assembly or negative pressure source 812 consisting of a DC motor drive 814, a pump 815 such as a diaphragm pump, and a battery 818 for powering the pump assembly. A filter 820 is disposed in an aspiration channel 822 of the applicator body 802 as described in previous variations. The treatment device 800 illustrated in FIG. 26 includes a proximal non-disposable component 825A and a distal replaceable component 825B that may be used a number of times (e.g., 1 to 50 times) before replacement. The proximal portion 825A carries the motor drive 814, the pump 815, the battery 818, an activation switch 826 and electronic circuitry on a circuit board 830 including a processor or controller 840 for controlling operating parameters of the device. The distal replaceable component 825B of FIG. 26 is configured with a spherical rolling member 845 as described previously carried in a housing 846 in the distal tip 810 which communicates with the aspiration channel 822 and filter 820 therein that in turn communicates with the negative pressure source 812. The distal component 825B also can be disassembled as described above to allow for cleaning and re-use of the rolling member 845 and cleaning or replacement of the filter 820.

In the variation of FIG. 26, the applicator 800 has an activation switch 826 positioned in the proximal component 825A for activating the negative pressure source 812, although such a switch 826 could be carried in the distal component 825B as will be described in the variation of FIG. 28. In one variation, the negative pressure source comprising a motor drive 814 and diaphragm pump 815 can be an AIMELIAE DC 3V Micro Vacuum Air Pump coupled to a Lipo #301120 3.7V 40 mAh rechargeable lithium-ion battery pack. FIG. 26 also shows that the applicator 800 has at least one exhaust port 852 for outflows from the negative pressure source 812.

Figure 27:
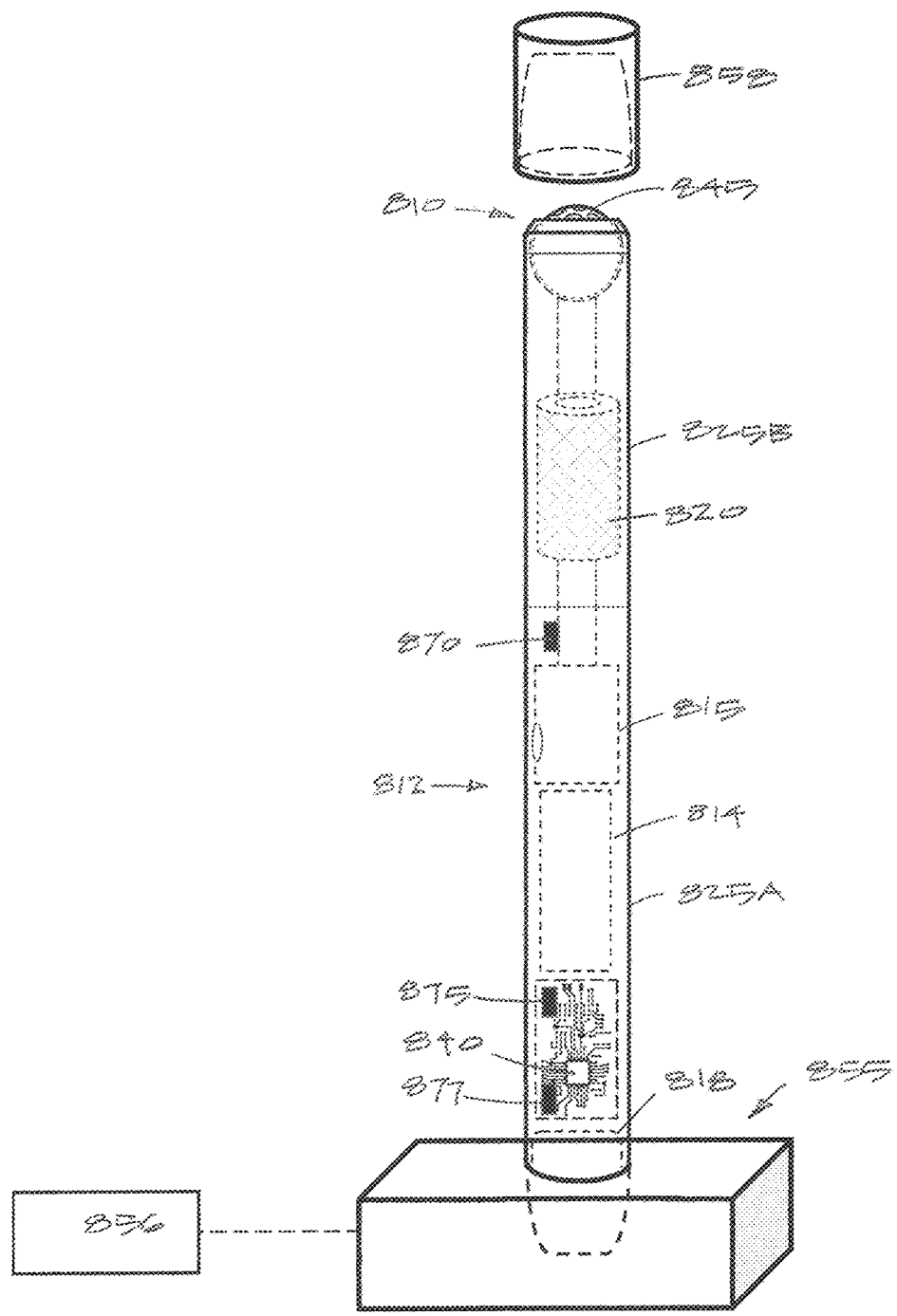
FIG. 27 is a view of the applicator of FIG. 26 inverted and shown inserted in base unit configured for recharging the battery.

FIG. 27 shows the applicator 800 of FIG. 26 in an inverted position and inserted into a base 855 connected to electrical source 856 that is adapted for inductively recharging the battery 818 as is known in the art. A removable cap 858 is shown for covering the distal tip 810 when not in use.

In one variation, the applicator 800 is adapted for lip treatments as illustrated in FIG. 26 and has an elongated applicator body 802 that has a cylindrical shape or an oval cross-section, with or without proximal and/or distal tapered regions, wherein the outer surface of applicator body 802 has a maximum diameter of 30 mm or less, 25 mm or less, or 20 mm or less. In this variation, the applicator body 802 has an axial length of 15 cm or less. These dimensions allow the applicator 800 to be carried conveniently by the subject in a pocket or purse.

The applicator 800 of FIG. 26 is adapted to be used in a method as described previously where the perimeter portion 860 of the distal tip 810 contacts targeted tissue and forms a seal against the targeted tissue. Negative pressure provided by the negative pressure source 812 then suctions a surface of the targeted tissue against the rolling member 845. The user then moves the distal end 810 over the targeted tissue, where the rolling number 845 reduces friction while contemporaneously manipulating the targeted tissue to enhance tissue permeability. At the same time, the negative pressure is distributed over an aspiration portion 862 of the distal tip 810 that is surrounded by perimeter portion 860 which forms the seal against the tissue. In this variation as in previous variations, the negative pressure is provided through a plurality of discreet apertures 865 in the aspiration portion 862. In this variation the apertures 865 extend through and around the rolling member 845 which are adapted to (i) reduce friction when moving the distal tip 810 over tissue, and to (ii) prevent excess negative pressure from interfacing with any overly larger surface portion of the targeted tissue which could grip the tissue surface and resist movement of the tip over such a tissue surface. The distribution of negative pressure over the plurality of apertures 865 further can prevent unwanted localized damage to microvasculature in subsurface tissue.

Referring to FIG. 26, the applicator 800 carries a processor or controller 840 for controlling operating parameters of negative pressure source 812 as well as other optional components described further below. In FIG. 26, it can be seen that the applicator 800 also carries a pressure sensor 870 exposed to the aspiration channel 822 in the applicator body for sensing negative pressure therein. In a variation, the pressure sensor 870 is adapted to sense negative pressure during use and send signals to the controller 840. The controller 840 then is configured to modulate the negative pressure source 812 to maintain a selected negative pressure within the applicator 800, or to de-activate the negative pressure source 812 if excessive negative pressure is sensed over a selected time interval.

Still referring to FIG. 26, the applicator 800 also carries at least one accelerometer 875 which allows for sensing the user's movement of the applicator 800. In one mode of operation, the accelerometer 875 can be adapted to sense non-movement of distal tip 810 over the targeted tissue and then send signals to the controller 840, wherein the controller 840 then modulates or de-activates the negative pressure source 812. This mode of operation can prevent the distal tip 810 from being suctioned against tissue when the direction of movement of the distal tip 810 is reversed.

In another variation (not shown) the perimeter portion 860 of the distal tip 810 can carry spaced apart electrical contacts coupled to the controller 840 and battery 818 to sense capacitance, impedance, or phase angle of an electrical current to allow for sensing tissue engagement by such electrical contacts. In this variation, the controller 840 then can activate the negative pressure source 812 upon sensed contact with tissue and de-activate the negative pressure source 812 upon loss of tissue contact. In another variation, the perimeter portion 860 of the distal tip 810 can carry one or more pairs of electrodes (see FIG. 32A) for delivering electrical current to a subject's skin or lips for electroporation or stimulus purposes.

In another variation, referring to FIG. 26, the controller 840 is configured to enable a mode of operation including a time-out feature that is adapted to de-activate the negative pressure source 812 after a selected interval of continuous use followed by a selected time-out interval. This mode of operation prevents the over-application of negative pressure to the targeted tissue. In another mode of operation, the controller 840 is configured to pulse the negative pressure source 812.

Figure 28:
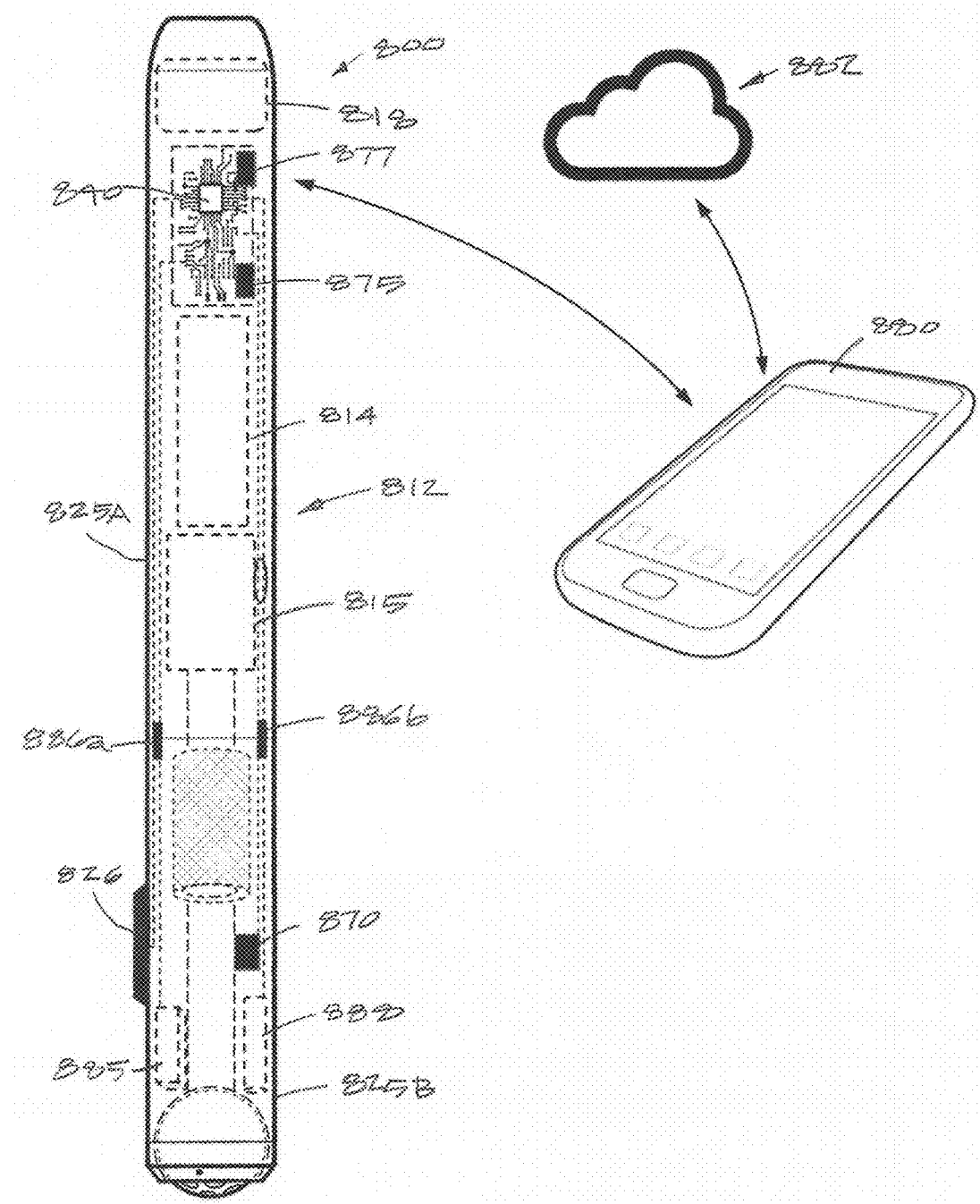
FIG. 28 is a transparent elevational view of another variation of applicator similar to that of FIG. 26 with an optional LED and an optional vibration mechanism further illustrating a blue-tooth component for wireless communication with a mobile device and the cloud.

Now referring to FIGS. 26 and 28, the applicator 800 also carries a Bluetooth transmitter-receiver 877 for communicating wirelessly with a remote mobile device 880 such as a cell phone or tablet where an app on the mobile device 880 is adapted to communicate with the controller 840 to adjust operating parameters of the applicator. Also, as can be seen in FIG. 28, the applicator 800 and mobile device 880 can communicate with the cloud 882 for storing data for analytic purposes. The operating parameters that can be adjusted within a first or default mode of operation include but are not limited to (i) a maximum allowable negative pressure during use, (ii) a targeted set pressure, (iii) a time interval of allowable excess negative pressure, (iv) a maximum interval of continuous use, (v) the length of a time-out interval, (vi) ON-OFF off the pulse rate of negative pressure, (vii) variability of pulse rate of negative pressure; (viii) time interval following accelerometer signals relating to lack of movement for modulating negative pressure, and (ix) manual activation of the negative pressure source or contact-based activation of the negative pressure source.

Further, the app on the mobile device 880 can be used to switch between other operating modes of the applicator 800. In one variation, a second mode of operation includes activating at least one LED 885 (FIG. 28) carried by the applicator 800 including a selection of operating parameters thereof including LED light intensity, LED wavelength, and continuous or pulsed activation of the LED 885.

Further, the app on the mobile device 880 can be used to switch to a third mode of operation which includes activating the at least one vibration mechanism 888 or ultrasound transducer carried by the applicator 800 including a selection of operating parameters thereof. Further, the app on the mobile device 880 can be used to switch to a fourth mode of operation which includes activating an electrical current delivery component of the applicator (see FIG. 32A) including a selection of operating parameters thereof.

Still referring to FIG. 28, it can be seen that electrical connectors 886a and 886b are provided between the proximal component 825A and the distal component 825B (see FIG. 26) to couple the activation switch 826, the LED 885, and the vibration mechanism 888 to the controller 840 and battery 818. Similar connectors (not shown) can be provided for and contact-sensing component and any electrical current delivery component as described above.

Figure 29:
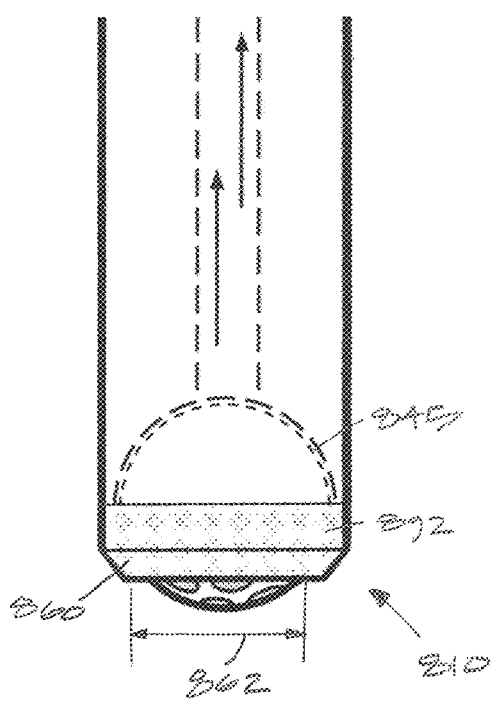
FIG. 29 is an enlarger view of the distal applicator tip of FIG. 26 with a rolling member showing a lubricious or absorbent perimeter portion of the distal tip.

Now turning to FIG. 29, an enlarged view of the distal tip 810 of the treatment device 800 of the FIG. 26 is shown where in the perimeter portion 860 of the distal tip 810 comprises a lubricious material or a flexible sponge-like material 892 that is adapted to absorb liquid treatment media and carry such treatment media over the targeted tissue during use. The perimeter portion 860 again surrounds the aspiration portion 862 that comprises the exposed surface of the rolling member 845.

In some variations, the treatment media TM (see FIG. 32A) includes at least one of a hyaluronic acid HA or derivative thereof, Vitamin E, Vitamin B3, retinol, *Mentha piperita* leaf, a peptide complex to support collagen production, and an irritant such as cinnamon, ginger, wintergreen, or bee venom. In one variation, a hyaluronic acid HA or derivative thereof is a key component of the treatment media as shown schematically in FIG. 32A. Hyaluronic acid is abundant in skin and lips of a human subject and is unique in that HA retains large amounts of moisture in the skin which in turn provides a plump and youthful appearance to a subject's skin or lips.

Figure 30:
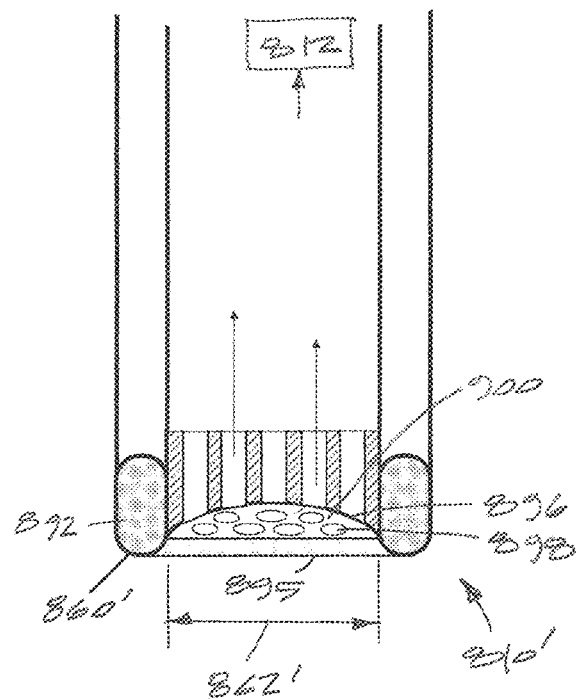
FIG. 30 is an enlarged view of an alternative distal tip of an applicator that has a plurality of apertures communicating with the negative pressure source.

FIG. 30 shows another variation of an applicator distal tip 810' without a rolling member that is configured with a lubricious perimeter portion 860' similar to that of FIG. 29. Alternatively, the perimeter portion 860' can be sponge-like material 892 as in the variation of FIG. 29. In the variation of FIG. 30, the perimeter portion 860' of the distal tip 810' has a planar distal-facing surface 895 wherein the aspiration portion 862' of the distal tip comprises a concavity 896 where negative pressure interfaces with targeted tissue. The aspiration portion 862' is configured with a plurality of apertures 898 having a diameter of less than 2.0 mm that communicate with the negative pressure source 812. Each of the apertures 898 is within a non-apertured field 900 of the aspiration portion 862'. By configuring the aspiration portion 862' with such apertures 898 and such a non-apertured field 900, the negative pressure is distributed evenly over all portions of the targeted tissue that interfaces with the distal tip 810' and prevents the aspiration portion 862' from being suctioned tightly against tissue, which would prevent effortless movement over targeted tissue. Typically, the distal tip of an applicator has a surface area of at least 25 mm². In one variation, the surface area of the distal tip is between 25 mm² and 125 mm² for an applicator configured for treating lips, whether it carries one or more rolling members or is of the type shown in FIG. 30.

Figures 31A, 31B:
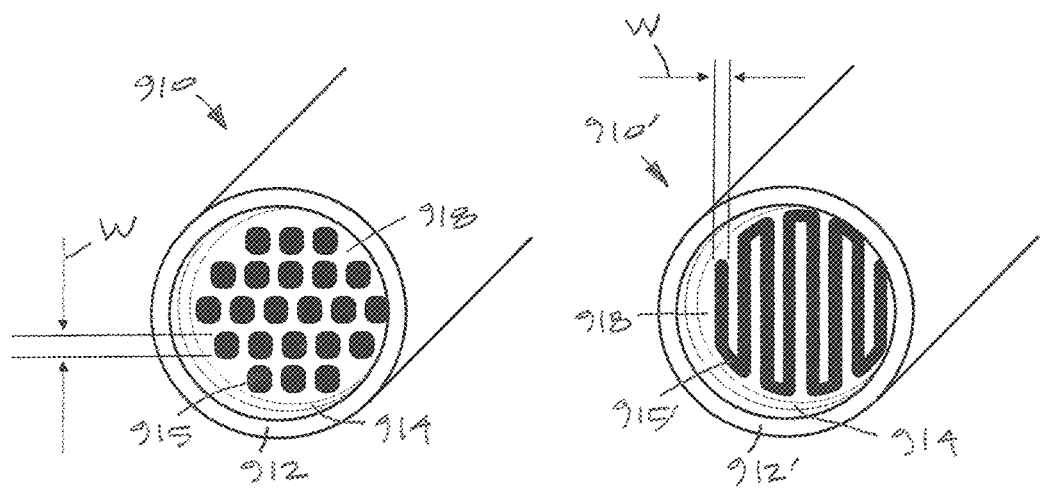
FIG. 31A is a perspective view of an applicator tip similar to that of FIG. 29 showing small diameter apertures in an aspiration portion of the tip.
FIG. 31B is a perspective view of another applicator tip configured with a narrow serpentine aperture.

FIG. 31A is a perspective view of a distal tip 910 similar to that of FIG. 30 where a perimeter portion 912 surrounds a concave aspiration portion 914 that is configured with a plurality of substantially round apertures 915 and a non-apertured field 918. In this variation, each aperture 915 has a width W or dimension of a minor axis of 2.0 mm or less. FIG. 31B is a perspective view of a distal tip 910' similar to that of FIG. 31A where a perimeter portion 912' surrounds a concave aspiration portion 914' with an aperture 915' comprising a serpentine slit within a non-apertured field 918. In this variation, the aperture 915' has a width W or dimension of a minor axis of 2.0 mm or less. As can be seen in FIGS. 31A and 31B, the apertures 915 and 915' are provided in all regions of each tip's aspiration portion 914 and 914' respectively to distribute exposure to negative pressure over corresponding discrete portions of the surface of targeted tissue, which prevents the tip from being suctioned firmly against the tissue surface.

Figure 32A:
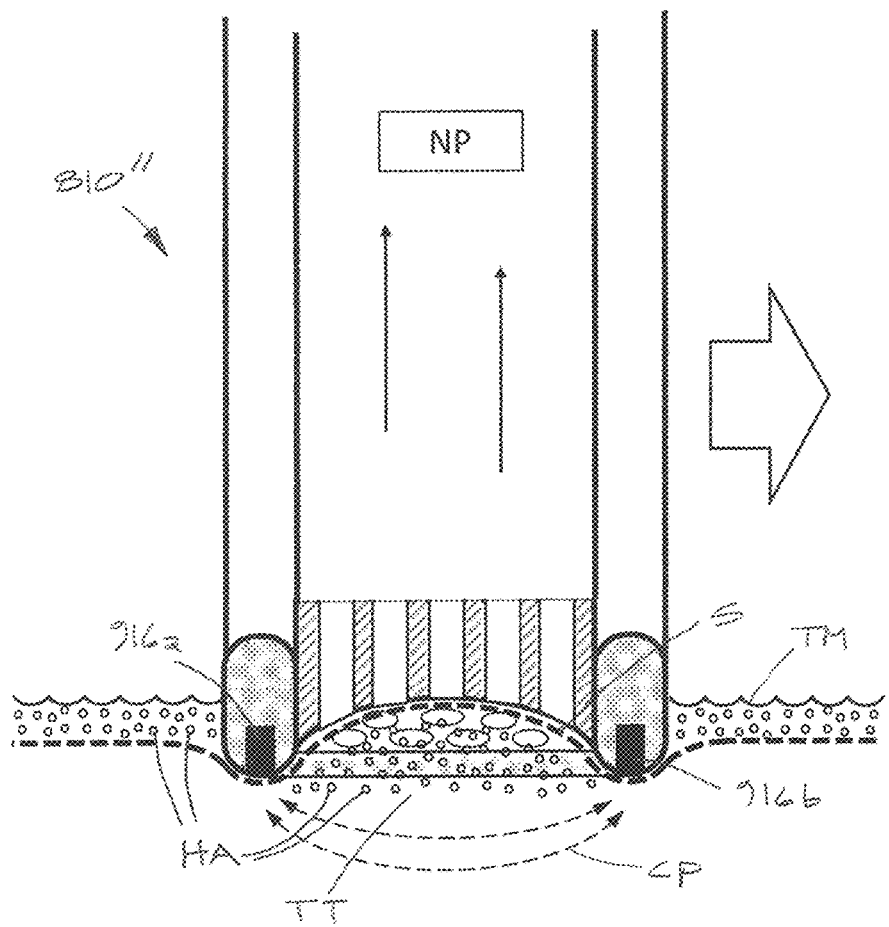
FIG. 32A is a schematic illustration of another variation of applicator tip that contemporaneously applies negative pressure and an electroporation current to a subject's lip or skin to cause transport of hyaluronic acid through the surface to subsurface tissue.

Now turning to FIG. 32A, a distal applicator tip 810" is shown with an electrode arrangement therein comprising electrodes 916a and 916b that are adapted to deliver a pulsatile electrical current in current paths CP to the targeted tissue TT to enhance transportation of hyaluronic acid HA into subsurface targeted TT tissue through the skin surface S by means of electroporation in combination the negative pressure as described above and below. The method of electroporation has been shown to create transient aqueous pores in cell membranes upon application of electrical pulses, typically comprising short duration high voltage pulses. During such electrical pulsing, molecules which would not normally penetrate skin can be transported through the skin surface S during the interval of induced, reversible permeability of skin surface membranes. The transdermal transport of molecules of different sizes including high molecular weight proteins, peptides, oligonucleotides, etc. is possible. In some variations, the method for delivering the pulsed current in current paths CP in FIG. 32A to the subject's lips or skin comprises applying a pulsed current having an average current density ranging from 0.01 mA/cm$^2$ to 20 mA/cm$^2$, a pulse width ranging from 5 microseconds to 1 millisecond, a plurality of pulsatile wave packets from 1 to 100 pulses, and frequency of such wave packets ranging from 5 Hertz to 1,000 Hertz.

Figure 32B:
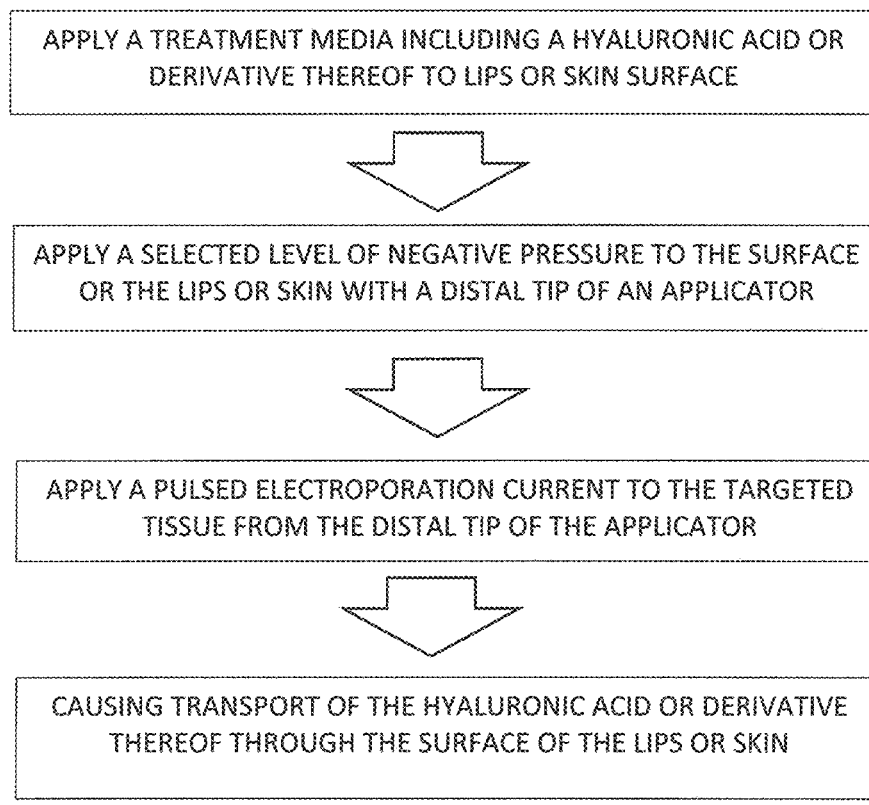
FIG. 32B is an illustration of the steps of the method of causing the transport of hyaluronic acid through the surface of skin or lips.

Referring to FIG. 32B, a method of treating a subject's lips or skin comprises topically applying a treatment media including a hyaluronic acid (HA) or derivative thereof to a targeted tissue of the subject's lips or skin, applying a selected level of negative pressure to the targeted tissue with a distal tip of an applicator, and applying a pulsed electroporation current to the targeted tissue wherein the selected level of negative pressure and the selected pulse parameters allow for to transport of the hyaluronic acid or derivative thereof through the surface of the targeted tissue to subsurface tissue. In this method, the negative pressure is applied to the tissue at the distal tip of an applicator at a selected level of negative pressure of at least negative 3.0 psi. In some variations of the method, the negative pressure at the surface S of the tissue is at least negative 4.0 psi. In another method variation, the negative pressure is at least negative 5.0 psi. In this method, the electrical current is pulsed with pulse widths ranging from 5 microseconds to 1 millisecond, where pulses are provided in wave packets of 1 to 100 pulses with a frequency of wave packets application ranging from 5 Hertz to 1,000 Hertz.

In general, a method for treating a subject's skin or lips with an applicator of the invention comprises (i) providing an applicator carrying a negative pressure source for causing negative pressure within the applicator, wherein a distal tip of the applicator has a perimeter portion surrounding an aspiration portion with at least one aperture therein, wherein the at least one aperture has a width or minor axis of 2.0 mm or less, wherein the at least one aperture is disposed in substantially all regions of the aspiration portion, and wherein the aspiration portion has a surface area of at least 25 mm$^2$, and (ii) contacting targeted tissue of a subject's skin or lips with the distal tip of the applicator, activating the negative pressure source and moving the distal tip over the targeted tissue to transiently cause negative pressure in subsurface tissue. A topical treatment media may be applied to the tissue surface before and during use. The negative pressure source 812 is configured to provide a negative pressure of at least negative 3.0 psi at the distal tip when in contact with tissue. In some variations of applicator, the negative pressure at the distal tip when in contact with tissue during use is at least negative 4.0 psi, and is some embodiments is at least negative 5.0 psi.

Figure 33:
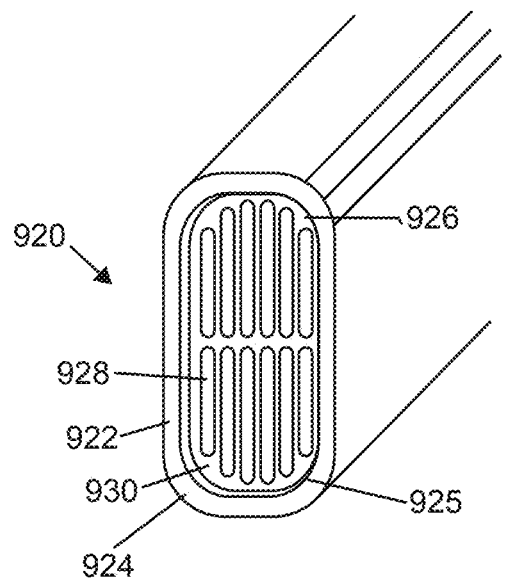
FIG. 33 is a perspective view of another applicator tip with a rectangular configuration and narrow apertures.

FIG. 33 illustrates a distal tip 920 of another variation of applicator where the perimeter portion 922 is rectangular and again has a planar distal-facing surface 924. The aspiration portion 925 of the distal tip 920 comprises a recessed region 926 where negative pressure can interface with targeted tissue. The aspiration portion 925 is configured with a plurality of elongate slit-type apertures 928 that communicate with the negative pressure source. Each of the slit-type apertures 928 is surrounded by a non-apertured field 930 of the aspiration portion 925 and each aperture 928 has a width W of 2.0 mm or less. In all variations herein, the width of any aperture is less than 2.0 mm and often 1.0 mm or less to distribute the negative pressure evenly over the targeted tissue and preventing tissue from being suctioned tightly against the distal tip.

Figures 34A, 34B:
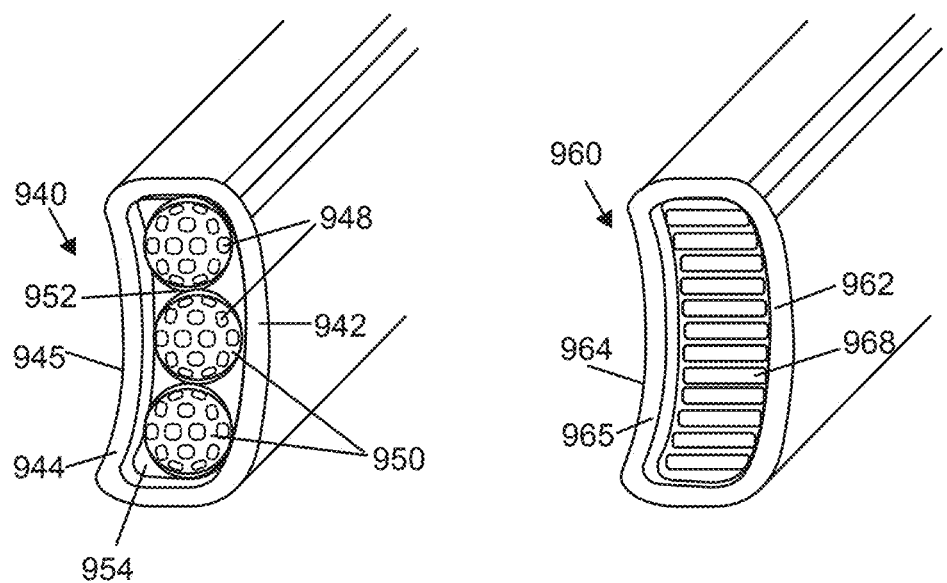
FIG. 34A is a perspective view of another applicator tip configured with a non-planar distal-facing periphery and a plurality of rolling members.
FIG. 34B is a view of another applicator tip with a non-planar distal-facing periphery and a plurality of narrow slit-type apertures.

FIG. 34 depicts another variation of an applicator distal tip 940 with a perimeter portion 942 having a rectangular shape with a distal-facing surface 944 that is non-planar and exhibits an inward curvature 945 that is adapted for improved contact with a subject's lips. In this variation, the plurality of apertures 948 comprise channels through multiple spherical rolling members 950 as well as spaces 952 adjacent and around the rolling members 950. Each of the spherical rolling members 950 can disposed in a housing 954 allowing for rolling of each rolling member 950 in any direction. In another variation, the rolling member 950 can be configured with an axle and ten can rotate in either rotational direction about such an axle (not shown).

Figure 35:
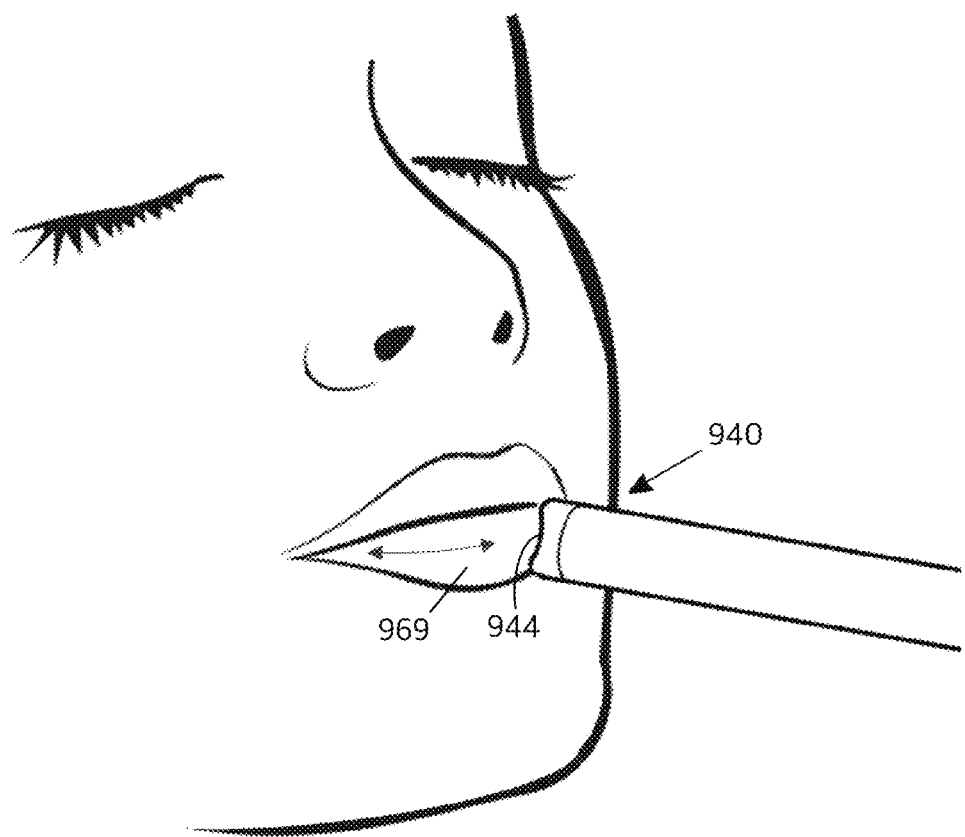
FIG. 35 is a view of an applicator tip configured with non-planar distal-facing periphery in use on a subject's lips.

FIG. 35 shows another variation of an applicator distal tip 960 that has a rectangular perimeter portion 962 with a non-planar distal-facing surface 964 and an inward curvature 965 adapted for treating lips. In this variation, the plurality of apertures comprises narrow slits 968 similar to the distal tip of FIG. 33. FIG. 35 illustrates a method of use of an applicator of the types in FIGS. 34A and 34B, such as tip 940 with a non-planar distal surface 944 having a curvature 945 that fits the curved shape of a subject's lips 969.

FIGS. 36 and 37 show other variations of applicator distal tips 970 and 980 with respective distal-facing surfaces that are non-planar and exhibit an inward curvature again adapted for contact with a subject's lips. In the variation of FIG. 36, an hour-glass shaped rolling member 982 is provided that rotates around a central axle 984. A plurality of apertures 985 comprising channels are provided in the rolling member 982 as well as spaces 986 adjacent to and around the rolling member 982. The perimeter portion 988 has an hour-glass shape around the rolling member 982. FIG. 37 illustrates a distal tip 980 with a plurality of rolling members 990 that rotate around portions of an axle 992. Again, a plurality of apertures 995 are provided in the rolling members 990 as well as in spaces 996 adjacent to and around the rolling members 990.

FIGS. 36 and 37 show other variations of applicator distal tips 970 and 980 with respective distal-facing surfaces that are non-planar and exhibit an inward curvature again adapted for contact with a subject's lips. In the variation of FIG. 36, an hour-glass shaped rolling member 982 is provided that rotates around a central axle 984. A plurality of apertures 985 comprising channels are provided in the rolling member 982 as well as spaces 986 adjacent to and around the rolling member 982. The perimeter portion 988 has an hour-glass shape around the rolling member 982. FIG. 37 illustrates a distal tip 980 with a plurality of rolling members 990 that rotate around portions of an axle 992. Again, a plurality of apertures 995 are provided in the rolling members 990 as well as in spaces 996 adjacent to and around the rolling members 990.

In other variations, an ultrasound wave generator such as a piezoelectric crystal can be provided in the distal tip of the applicator to deliver pressure waves at ultrasonic speeds to the skin, for example, in the range of 1 Mhz to 6 Mhz to enhance fluid absorption. In another variation, the working end can include components and electrodes for delivering electrical current through the rolling member or the distal periphery of the roller housing to the skin of a patient to enhance fluid penetration. In a further variation, the LEDs as in FIG. 11 can transmit UV light to kill bacteria.

While the invention has been described for delivery of treatment media to a subject's skin and lips largely for skin rejuvenation and cosmetic purposes, the negative pressure applicator can also be used for enhancing delivery of any type of pharmaceuticals through an exposed tissue surface, such as analgesics, anti-inflammatory drugs, vaccines, stimulants, hormones and the like.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for treating a targeted tissue comprising a skin or a lip of a subject, comprising:
    providing an applicator carrying a negative pressure source capable of applying a negative pressure within the applicator, wherein a distal tip of the applicator has a perimeter portion surrounding a recessed region having a plurality of rolling members each being spherical and each located in a space in the recessed region, the plurality of rolling members are also configured to roll in any direction, the plurality of rolling members each having a plurality of channels formed therein forming an aspiration portion, the distal tip further comprising a low friction surface surrounding the recessed region;
    contacting the targeted tissue of the skin or the lip with the distal tip of the applicator while maintaining the low friction surface against the targeted tissue; and
    applying the negative pressure and moving the distal tip over the targeted tissue while maintaining the low friction surface against the targeted tissue to transiently cause negative pressure in a subsurface tissue where the low friction surface permits movement of the distal tip against the targeted tissue.

2. The method of claim 1 further comprising rolling the plurality of rolling members against tissue to further assist in movement of the distal tip over the targeted tissue.

3. The method of claim 1 wherein the low friction surface comprises a lubricious material located on the perimeter portion.

4. The method of claim 1 wherein the distal tip further includes at least one electrode, the method further comprising applying a current into the targeted tissue to cause electroporation of the targeted tissue thereby increasing permeability and allowing passage of a substance through a surface of the targeted tissue.

5. The method of claim 4, wherein the substance is applied to the surface of the targeted tissue, and the substance comprises a hyaluronic acid.

6. The method of claim 1 further comprising controlling the negative pressure with a controller in the applicator coupled to a negative pressure source.

7. The method of claim 6, wherein the controller is responsive to signals from a pressure sensor carried by the applicator that senses negative pressure within the applicator during use.

8. The method of claim 6, wherein the controller is configured to control the negative pressure source to maintain a selected negative pressure within the applicator during use.

9. The method of claim 6, wherein the controller is responsive to signals from an accelerometer carried by the applicator to modulate or terminate negative pressure in the applicator during use when lack of movement is detected.

10. The method of claim 6, wherein the controller is configured with a time-out feature that stops the negative pressure source after a selected interval of use followed by a selected time-out interval after which the negative pressure source may be activated.

11. The method of claim 6, wherein the controller is configured to pulse the negative pressure source.

12. The method of claim 6, further comprising using a mobile electronic device to communicate with the controller through a wireless connection to a Bluetooth receiver carried by the applicator to adjust operating parameters of the applicator.

13. The method of claim 1 further comprising using a Bluetooth transmitter carried by the applicator to transmit operating data to a remote electronic device or a cloud storage.

14. The method of claim 1 further comprising applying a topical treatment media to a surface of the targeted tissue.

15. A device for treating a targeted tissue comprising a skin or a lip of a subject, comprising:
    an applicator body carrying a negative pressure source for providing a negative pressure within the applicator body; and
    a distal tip of the applicator body having a perimeter portion configured for contacting the targeted tissue, wherein the perimeter portion surrounds a recessed region having a plurality of rolling members each being spherical and each rolling member located in a space within the recessed region and where the plurality of rolling members are configured to roll in any direction, the plurality of rolling members each having a plurality of channels formed therein forming an aspiration portion, the aspiration portion having a plurality of apertures distributed over the aspiration portion such that a surface of the aspiration portion between the plurality of apertures comprises a non-apertured field, and wherein the plurality of apertures are configured to apply the negative pressure to the targeted tissue; and
    wherein the plurality of apertures are distributed over the aspiration portion to distribute the negative pressure over all regions of the aspiration portion exposed in the perimeter portion that interface with the targeted tissue.

16. The device of claim 15, further comprising at least one electrode configured to apply current to the targeted tissue to cause electroporation or stimulation of the targeted tissue.

17. The device of claim 15, wherein moving the distal tip over the targeted tissue causes rotation of the plurality of rolling members against tissue and reduces friction between the distal tip and the targeted tissue.

18. The device of claim 15, wherein the perimeter portion comprises a lubricious material.

19. The device of claim 15, wherein the perimeter portion comprises a sponge-like material.

20. The device of claim 15, further comprising a controller carried by the applicator body for controlling operating parameters of the negative pressure source.

* * * * *